US011207369B2

(12) United States Patent
Zahid et al.

(10) Patent No.: US 11,207,369 B2
(45) Date of Patent: Dec. 28, 2021

(54) COMPOSITIONS AND METHODS FOR MODULATING CILIOGENESIS

(71) Applicant: UNIVERSITY OF PITTSBURGH-OF THE COMMONWEALTH SYSTEM OF HIGHER EDUCATION, Pittsburgh, PA (US)

(72) Inventors: Maliha Zahid, Gibsonia, PA (US); Cecilia Wen Ya Lo, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 74 days.

(21) Appl. No.: 16/473,731

(22) PCT Filed: Jan. 3, 2018

(86) PCT No.: PCT/US2018/012188
§ 371 (c)(1),
(2) Date: Jun. 26, 2019

(87) PCT Pub. No.: WO2018/129046
PCT Pub. Date: Jul. 12, 2018

(65) Prior Publication Data
US 2019/0336563 A1 Nov. 7, 2019

Related U.S. Application Data

(60) Provisional application No. 62/441,818, filed on Jan. 3, 2017.

(51) Int. Cl.
C07D 243/12 (2006.01)
A61K 47/64 (2017.01)
A61K 38/05 (2006.01)
A61P 11/06 (2006.01)

(52) U.S. Cl.
CPC ............... *A61K 38/05* (2013.01); *A61P 11/06* (2018.01)

(58) Field of Classification Search
None
See application file for complete search history.

(56) References Cited

U.S. PATENT DOCUMENTS

2006/0264380 A1* 11/2006 Hellstrom .......... A61K 38/1825
514/1.9

OTHER PUBLICATIONS

Kloe et al. (Small Molecules That Inhibit Notch Signaling, chptr. 23, Hugo J. Bellen and Shinya Yamamoto (eds.), Notch Signaling: Methods and Protocols, Methods in Molecular Biology, vol. 1187 (2014) (Year: 2014).*
DAPT Pubchem, accessed at Apr. 24, 2021 at URL pubchem.ncbi.nlm.nih.gov/compound/Dapt (Year: 2021).*
International Search Report and Written Opinion dated Mar. 26, 2018, from International Application No. PCT/US2018/012188, 9 pages.
Gerovac, et al. "Subermsion and Hypoxia Inhibit Ciliated Cell Differentiation in a Notch-Dependent Manner", American Journal of Respiratory Cell and Molecular Biology, Apr. 22, 2014, vol. 51, pp. 516-525.
Tilley, et al. "Cilia Dysfunction in Lung Disease", Annual Review of Physiology, Oct. 29, 2014, vol. 77, pp. 379-406.
Konishi, et al. "Directed Induction of Functional Multi-ciliated Cells in Proximal Airway Epithelial Spheroids from Human Pluripotent Stem Cells", Stem Cell Reports, Jan. 12, 2016, vol. 6, pp. 18-25.
Stasiulewicz, et al. "A conserved role for Notch signaling in priming the cellular response to Shh through ciliary localisation of the key Shh transducer Smo", Development, Jul. 1, 2015, vol. 142, pp. 2291-2303.
Firth, a. et al. "Generation of multiciliated cells in functional airway epithelia from human induced pluripotent stem cells", PNAS< Mar. 24, 2014, E1723-E1730.
Shapiro, et al., "Laterality defects other than situs inversus totalis in primary ciliary dyskinesia: insights into situs ambiguus and heterotaxy". Chest, 2014, 146:1176-1186.
Li, Y. et al. Global genetic analysis in mice unveils central role for cilia in congenital heart disease. Nature 521, 520-524, doi:10.1038/nature14269 (2015).
Garrod, et al., "Airway Ciliary Dysfunction and Sinopulmonary Symptoms in Patients with Congenital Heart Disease", Ann. Am. Thorac. Soc., 2014, 11:1426-32.
Stewart, et al., "Airway ciliary dysfunction: Association with adverse postoperative outcomes in nonheterotaxy congenital heart disease patients", J of Thoracic and Cardiovas Surgery, 2017, 17:31968-2.
Swisher, et al., "Increased postoperative and respiratory complications in patients with congenital heart disease associated with heterotaxy", J. Thorac. Cardiovasc. Surg., 2011, 141:637-44.
Li, et al. "Respiratory Motile Cilia Dysfunction in a Patient with Cranioectodermal Dysplasia", Am J Med Genet, 2015, A 167A:2188-219.
Mathers, et al., "Projections of Global Mortality and Burden of Disease from 2002 to 2030", PLoS Med., 2006, 3:e442.

(Continued)

*Primary Examiner* — Julie Ha
*Assistant Examiner* — Kristina M Hellman
(74) *Attorney, Agent, or Firm* — Meunier Carlin & Curfman LLC

(57) ABSTRACT

Disclosed herein are methods for modifying ciliogenesis in one or more cells of a subject, the method comprising administering to the subject an effective amount of a composition comprising a Notch signaling inhibitor, wherein the modification results in an increase in a number of cilia, an increase in a length of cilia, and/or an increase in a beat frequency of cilia as compared to a control. Also disclosed herein are methods for modifying ciliogenesis in one or more cells of a subject, the method comprising administering to the subject from 0.1 µg/kg to 100 g/kg of a Notch signaling inhibitor. In some embodiments, the methods can be used to treat Chronic Obstructive Pulmonary Disease (COPD), Emphysema, Asthma, Primary Ciliary Dyskinesia (PCD), Cystic Fibrosis (CF), or hydrocephalus.

20 Claims, 14 Drawing Sheets

(56) References Cited

OTHER PUBLICATIONS

McLean, et al., "Projecting the COPD population and costs in England and Scotland: 2011 to 2030", Scientific Reports, 2016, 6:31893.

Hoogendoorn, et al., "Developing and Applying a Stochastic Dynamic Population Model for Chronic Obstructive Pulmonary Disease", Value in health: J. Inti. Soc. Pharmacoeconomics Outcomes Res., 2011, 14:1039-47.

Astudillo et al., "The Small Molecule IMR-1 Inhibits the Notch Transcriptional Activation Complex to Suppress Tumorigenesis", Cancer Res., 2016, 76(12):3593-603.

Karp, et al., "An In Vitro Model of Differentiated Human Airway Epithelia", Methods Mol. Biol., 2002, 188:115-137.

Shapiro, et al., "Diagnosis, Monitoring, and Treatment of Primary Ciliary Dyskinesia: PCD Foundation Consensus Recommendations Based on State of the Art Review", Pediatr. Pulmonol., 2016, 51:115-132.

Ito, et al., "Hypoxia-Inducible Factor Regulates Expression of Surfactant Protein in Alveolar Type II Cells In Vitro", Am. J. Respir. Cell Mol. Biol., 2011, 45:938-945.

Schindelin, et al., "Fiji: an open-source platform for biological-image analysis", Nat. Methods, 2012, 9:676-682.45.

Doube, et al., "BoneJ: free and extensible bone image analysis in ImageJ", Bone, 2010, 47:1076-1079.

Strutz, et al., "Identification and Characterization of a Fibroblast Marker: FSP1", J. Cell Biol., 1995, 130:393-405.

You, et al., "Growth and differentiation of mouse tracheal epithelial cells: selection of a proliferative population", Am. J. Physiol. Lung Cell Mol. Physiol., 2002, 283:L1315-1321.

Jorissen, M., Van der Schueren, B., Van den Berghe, H. & Cassiman, J. J. The preservation and regeneration of cilia on human nasal epithelial cells cultured in vitro. Arch Otorhinolaryngol 246, 308-314 (1989).

Jorissen, M. & Bessems, A. Normal ciliary beat frequency after ciliogenesis in nasal epithelial cells cultured sequentially as monolayer and in suspension. Acta Otolaryngol 115, 66-70 (1995).

Tan, S. Y. et al. Heterotaxy and complex structural heart defects in a mutant mouse model of primary ciliary dyskinesia. J Clin Invest 117, 3742-3752, doi:10.1172/JCI33284 (2007).

Guseh, J. S. et al. Notch signaling promotes airway mucous metaplasia and inhibits alveolar development. Development 136, 1751-1759, doi:10.1242/dev.029249 (2009).

Tsao, P. N. et al. Notch signaling controls the balance of ciliated and secretory cell fates in developing airways. Development 136, 2297-2307, doi:10.1242/dev.034884 (2009).

Nonaka, S. et al. Randomization of left-right asymmetry due to loss of nodal cilia generating leftward flow of extraembryonic fluid in mice lacking KIF3B motor protein. Cell 95, 829-837 (1998).

Fliegauf, M., Benzing, T. & Omran, H. When cilia go bad: cilia defects and ciliopathies. Nat Rev Mol Cell Biol 8, 880-893, doi:10.1038/nrm2278 (2007).

Horani, A., Dickinson, J. D. & Brody, S. L. Applications of mouse airway epithelial cell culture for asthma research. Methods Mol Biol 1032, 91-107, doi;10.1007/978-1-62703-496-8_7 (2013).

Rojas, M. et al. Bone marrow-derived mesenchymal stem cells in repair of the injured lung. Am J Respir Cell Mol Biol 33, 145-152, doi:10.1165/rcmb.2004-0330OC (2005).

Bellusci, S. et al. Involvement of Sonic hedgehog (Shh) in mouse embryonic lung growth and morphogenesis. Development 124, 53-63 (1997).

Pepicelli, C. V., Lewis, P. M. & McMahon, A. P. Sonic hedgehog regulates branching morphogenesis in the mammalian lung. Curr Biol 8, 1083-1086 (1998).

\* cited by examiner

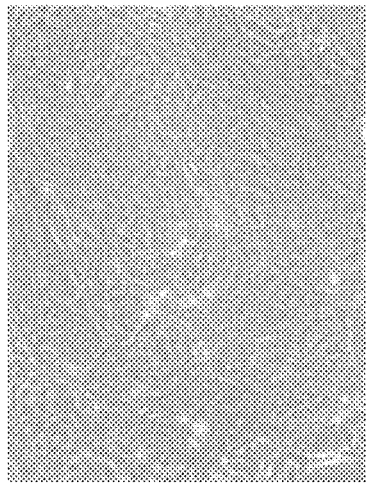
FIG. 1C
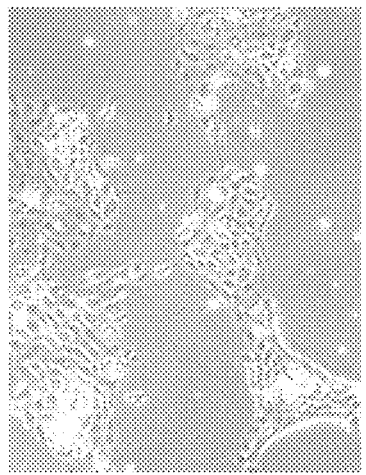
FIG. 1F
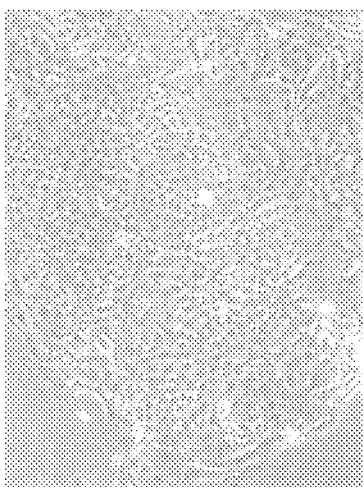
FIG. 1B
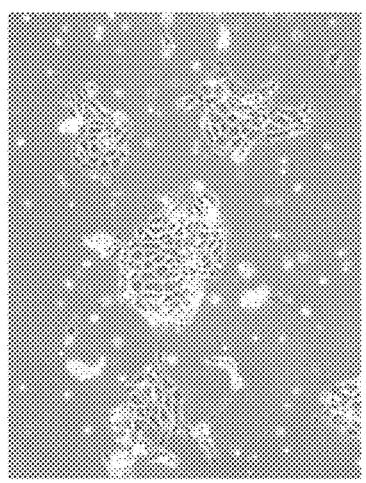
FIG. 1E
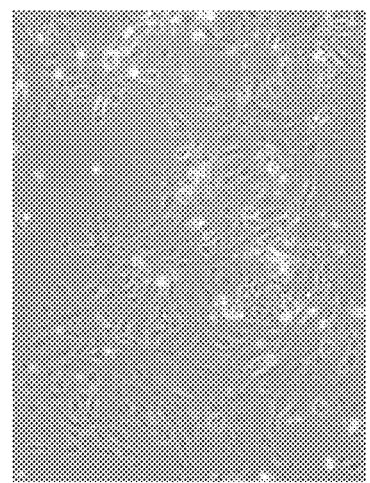
FIG. 1A
FIG. 1D

COMPOSITIONS AND METHODS FOR MODULATING CILIOGENESIS

CROSS REFERENCE TO RELATED APPLICATIONS

This application is a national stage application filed under 35 U.S.C. § 371 of PCT/US2018/012188, filed Jan. 3, 2018, that claims the benefit of U.S. Provisional Patent Application Ser. No. 62/441,818 filed Jan. 3, 2017, which are each expressly incorporated herein by reference.

FIELD

The present invention relates generally to compositions and methods for modulating ciliogenesis. Various parameters of ciliogenesis can be improved by the compositions and methods including, for example, ciliation, cilia length, and/or cilia beat frequency. The compositions and methods can be used to treat various ciliopathies and other cilia-related diseases.

BACKGROUND

Cilia are micro-tubule based essential cellular organelles present on every eukaryotic cell. Their roles in transcriptional regulation, cell cycle and motility continue to evolve and has generated intense interest over the past several decades. Cilia can be primary with a 9+0 microtubule structure or motile with 9+2 architecture. Over 200 genes are required to complete the complex process of ciliogenesis.

Cilia can be nonmotile, referred to as primary cilia, or motile such as in multiciliated respiratory epithelia or brain ependymal cilia. Coordinated, metachronal waves of motile cilia in the airway and ependyma generate directional fluid flow. Such motile ciliary function plays a key role in myriad functions ranging from airway protection, fertility and breaking of left-right symmetry.

The health of the respiratory tract requires the mucus clearance function provided by ciliated cells that line the airway. The cilia or hair-like projections on these cells are motile and serve an important airway defense mechanism by sweeping foreign matter, microbial contaminant and mucus out of the airway. Environmental insults, especially tobacco abuse, genetic mutations, or aging can reduce or compromise such motile cilia function in the airway, and lead to respiratory illness and degenerative lung disease, as seen in Chronic Obstructive Pulmonary Disease (COPD), Asthma, Primary Ciliary Dyskinesia (PCD), hydrocephalous, cystic fibrosis (CF), and also left-right patterning defects known as heterotaxy. Further, patients with congenital heart disease have been shown to have a high prevalence of abnormal respiratory ciliary motion associated with increased respiratory pathology. As motile cilia also play an important role in establishing the left-right body axis, PCD patients can exhibit situs anomalies, such as situs *inversus* totalis as in Kartagener's syndrome or heterotaxy (Shapiro, et al., *Chest*, 2014, 146:1176-1186). Those with heterotaxy typically have complex congenital heart disease (CHD), a reflection of the important role of left-right patterning in cardiac morphogenesis (Li, et al., Nature, 2015, 521:520-524; Tan, et al., *J. Clin. Invest.*, 2007, 117:3742-52). A high prevalence of motile ciliary dysfunction occurs in patients with complex CHD associated with heterotaxy (Garrod, et al., *Ann. Am. Thorac. Soc.*, 2014, 11:1426-32; Stewart, et al., *J of Thoracic and Cardiovas Surgery,* 2017, 17:31968-2). This is correlated with a high prevalence of chronic respiratory symptoms and disease (Garrod, et al., *Ann. Am. Thorac. Soc.,* 2014, 11:1426-32), and also increased post-operative pulmonary morbidity (Swisher, et al., *J. Thorac. Cardiovasc. Surg.*, 2011, 141:637-44). Recently a high prevalence of ciliary dysfunction was also shown in CHD patients without heterotaxy (Zahid et. Al. Manuscript submitted). This was similarly associated with increased respiratory symptoms and disease (Garrod, et al., *Ann. Am. Thorac. Soc.*, 2014, 11:1426-32). Together these findings suggest ciliary dysfunction may play an important in the pathogenesis of CHD. It is worth noting that mutations thought to affect largely primary cilia, can also perturb motile cilia function due to the fact that 75% of genes required for primary cilia are also expressed in motile cilia. Hence patients with ciliopathies, diseases mostly associated with cilia mutations thought to involve only the primary cilia defect, also may have motile cilia defects (Li, et al. *Am J Med Genet,* 2015, A 167A:2188-2196).

As understanding of the many roles of primary/motile cilia in development and disease continue to expand, so does interest in the basic biology of ciliogenesis. Mouse mutants have served as valuable models for studying various human ciliopathies, including PCD. This has accelerated insight into the role of ciliary dysfunction in human disease pathogenesis. Such studies are high priority given that pulmonary pathologies are now the third leading cause of death worldwide (Mathers, et al., *PLoS Med.*, 2006, 3:e442), and are projected to increase in the coming decades (McLean, et al., *Scientific Reports,* 2016, 6:31893; Hoogendoorn, et al., *Value in health: J. Intl. Soc. Pharmacoeconomics Outcomes Res.,* 2011, 14:1039-47).

SUMMARY

Disclosed herein are methods for modifying ciliogenesis in one or more cells of a subject, the method comprising administering to the subject an effective amount of a composition comprising a Notch signaling inhibitor, wherein the modification results in an increase in a number of cilia, an increase in a length of cilia, and/or an increase in a beat frequency of cilia as compared to a control. In some embodiments, the number of cilia on the one or more cells is increased by at least 25%. In some embodiments, the length of cilia is increased by at least 20%. In some embodiments, the beat frequency of cilia is increased by at least 15%. In some embodiments, the Notch signaling inhibitor comprises a gamma secretase inhibitor or a RBP-Jκ inhibitor. In some embodiments, the Notch signaling inhibitor is a gamma-secretase inhibitor selected from the group consisting of a dipeptide class, sulfonamide class, transition state mimic class, benzodiazepine class, benzocaprolactam class gamma-secretase inhibitor, and combinations thereof. In some embodiments, the Notch signaling inhibitor is selected from the group consisting of DAPT (N—[N-(3,5-Difluoro-phenacetyl-L-alanyl)]-S-phenylglycine t-butyl ester), 1-(S)-endo-N-(1,3,3)-Trimethylbicyclo[2.2.1]hept-2-yl)-4-fluoro-phenyl Sulfonamide, WPE-III31C, S-3-[N'-(3,5-difluorophenyl-alpha-hydroxyacetyl)-L-alanilyl]amino-2,3-dihydro-1-methyl-5-phenyl-1H-1,4-benzodiazepin-2-one, (N)—[(S)-2-hydroxy-3-methyl-butyryl]-1-(L-alaninyl)-(S)-1-amino-3-methyl-4,5,6,7-tetrahydro-2H-3-benzazepin-2-one, and combinations thereof. In some embodiments, the increase in the number of cilia, the increase in the length of cilia, and/or the increase in the beat frequency of cilia is achieved in nine days or less. In some embodiments, from 0.1 µg/kg to 100 g/kg of the Notch signaling inhibitor is administered to the subject. In some embodiments, the one or more cells is an epithelial cell. In some embodiments, the one or more cells are mesenchymal stem cells. In some embodiments, the one or more cells of a subject comprises a multitude of cells of a subject, and wherein the increase in the number of cilia, the increase in the length of cilia, and/or the increase in the beat frequency of cilia is determined based on an average obtained from the multitude of cells of a subject. In some embodiments, the subject is a human. In some embodiments, the subject has Chronic Obstructive Pulmonary Disease (COPD), Emphysema, Asthma, Primary Ciliary Dyskinesia (PCD), Cystic Fibrosis (CF), or hydrocephalus.

Also disclosed herein are methods for modifying ciliogenesis in one or more cells of a subject, the method comprising administering to the subject from 0.1 µg/kg to 100 g/kg of a Notch signaling inhibitor. In some embodiments, the method results in an increase in a number of cilia, an increase in a length of cilia, and/or an increase in a beat frequency of cilia as compared to a control. In some embodiments, the Notch signaling inhibitor comprises a gamma secretase inhibitor or a RBP-Jκ inhibitor. In some embodiments, the increase in the number of cilia, the increase in the length of cilia, and/or the increase in the beat frequency of cilia is achieved in nine days or less. In some embodiments, the one or more cells is an epithelial cell. In some embodiments, the one or more cells is a mesenchymal stem cell. In some embodiments, the subject is a human. In some embodiments, the subject has Chronic Obstructive Pulmonary Disease (COPD), Emphysema, Asthma, Primary Ciliary Dyskinesia (PCD), Cystic Fibrosis (CF), or hydrocephalus.

DESCRIPTION OF DRAWINGS

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are explanatory only and are not restrictive of the disclosure.

The accompanying drawings, which are incorporated in and constitute a part of this specification, illustrate certain examples of the present disclosure and together with the description, serve to explain, without limitation, the principles of the disclosure.

FIGS. 1(A-F) are micrographs of mouse tracheal epithelial cells (MTECs) in adherent stationary culture on rat-tail collagen coated 6-well culture dishes. MTECs were photographs on Days 0 (FIG. 1A), 2 (FIG. 1B), 3 (FIG. 1C), 5 (FIG. 1D), 6 (FIG. 1E), and 8 (FIG. 1F). In about 24-48 hours, the cells become adherent, loose their cilia, dedifferentiate and start expanding (FIG. 1B). Confluence is achieved in about 7-10 days (FIG. 1F).

FIGS. 2(A-C) are micrographs showing the quantification of reciliation using ImageJ program.

DETAILED DESCRIPTION

Figure 2A:
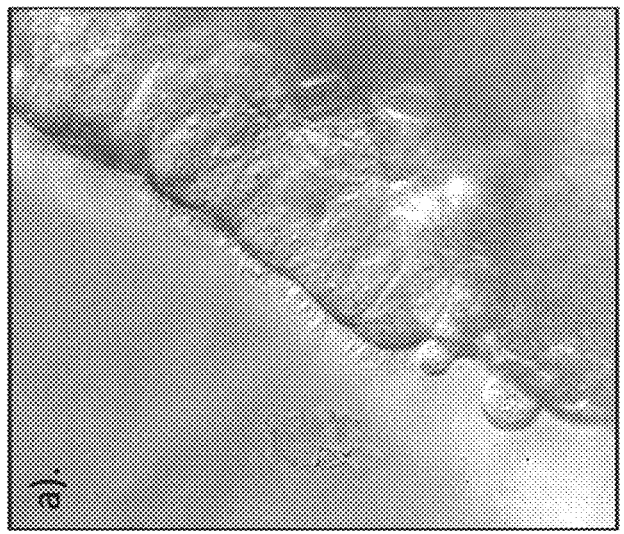
FIG. 2A: Video clips of reciliated mouse tracheal epithelial cells (MTECs) were used to capture a single still frame in ImageJ. The still frames showed a magnified view of the spheroid surface, which displayed ciliated and unciliated zones along the surface.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

The following definitions are provided for the full understanding of terms used in this specification. Unless defined otherwise, all technical and scientific terms used herein have the same meaning as commonly understood to one of ordinary skill in the art to which this disclosure belongs.

The term "comprising" and variations thereof as used herein is used synonymously with the terms "including," "containing," and variations thereof and are open, non-limiting terms. Although the terms "comprising," "including," and "containing" have been used herein to describe various embodiments, the terms "consisting essentially of" and "consisting of" can be used in place of "comprising," "including," and "containing" to provide for more specific embodiments and are also disclosed.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to the compound are discussed, specifically contemplated is each and every combination and permutation of the compound and the modifications that are possible unless specifically indicated to the contrary. Thus, if a class of compounds A, B, and C are disclosed as well as a class of compounds D, E, and F and an example of a combination compound, or, for example, a combination compound comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In some non-limiting embodiments, the terms are defined to be within 10% of the associated value provided. In some non-limiting embodiments, the terms are defined to be within 5%. In still other non-limiting embodiments, the terms are defined to be within 1%.

"Administration" to a subject includes any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering either or both a therapeutically effective amount and a prophylactically effective amount. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

Derivatives of the herein disclosed compounds include salts and pharmaceutically acceptable salts. "Pharmaceutically acceptable salts" include compounds derived from a parent compound that is modified by making an acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$-COOH where n is 0-4, and the like. The pharmaceutically acceptable salts of can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two.

"Therapeutically effective amount" or "therapeutically effective dose" of a composition (e.g. a composition comprising an agent) refers to an amount that is effective to achieve a desired therapeutic result or treatment. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

"Treat," "treating," "treatment," and grammatical variations thereof as used herein, include the administration of a composition with the intent or purpose of partially or completely delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. In some embodiments, a treatment reduces the severity of or ameliorates COPD, PCD, CF, and/or hydrocephalus. In some embodiments, a treatment improves the treated subject's pulmonary function test results. In some embodiments, a treatment improves the treated subject's spirometry results. In some embodiments, a treatment reduces the amount of water and/or cerebral spinal fluid in the brain. Treatments according to the invention may be applied prophylactically, palliatively or remedially. Prophylactic treatments are administered to a subject prior to onset (e.g., before obvious signs of COPD), during early onset (e.g., upon initial signs and symptoms of COPD), or after an established development of COPD. Prophylactic administration can occur for day(s) to years prior to the manifestation of symptoms of an infection.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Methods to Modulate Ciliogenesis

Described herein are methods for modifying ciliogenesis in one or more cells of a subject. The methods can treat a range of ciliary diseases or defects due to cilia damage by modifying ciliogenesis. The methods can improve one or more parameters of ciliogenesis, for example the overall coverage of a cell or tissue with cilia (also referred to as ciliation), the length of cilia, and/or the beat frequency of cilia. The novel methods include use of a notch signaling inhibitor to modify ciliogenesis, thereby achieving these beneficial outcomes.

Disclosed herein are methods for modifying ciliogenesis in one or more cells of a subject, the method comprising administering to the subject an effective amount of a composition comprising a Notch signaling inhibitor, wherein the modification results in an increase in a number of cilia, an increase in a length of cilia, and/or an increase in a beat frequency of cilia as compared to a control.

Also disclosed herein are methods for modifying ciliogenesis in one or more cells of a subject, the method comprising administering to the subject from 0.1 µg/kg to 100 g/kg of a Notch signaling inhibitor.

Also disclosed herein are methods for treating a disease in a subject, the methods comprising administering to the subject an effective amount of a composition comprising a Notch signaling inhibitor, wherein the modification results in an increase in a number of cilia, an increase in a length of cilia, and/or an increase in a beat frequency of cilia as compared to a control.

Also disclosed herein are methods for treating a disease in a subject, the method comprising administering to the subject from 0.1 µg/kg to 100 g/kg of a Notch signaling inhibitor.

Ciliogenesis is defined herein as the process of producing or improving qualities or functions of cellular cilia. Ciliogenesis is a highly regulated, ordered process which naturally cycles along with the cell cycle. Ciliogenesis in cells which perform different functions can result in different characteristics of cilia thought to affect ciliary function. For instance, length of cilia may be associated with ability to sweep fluid across the cell surface. Compared to some other ciliated cells, airway epithelial cells typically have longer cilia and/or higher ciliary beat frequencies to generate effective sweeping motions, thereby facilitating fluid flow.

Notch proteins comprise a family of transmembrane receptors known to modulate differentiation of respiratory, neuronal, and other cell types. Details are emerging regarding the role of Notch signaling in ciliogenesis. Disclosed herein are methods to inhibit notch signaling, thereby modifying ciliogenesis in a subject.

The Notch signaling inhibitor can be any one or more of an array of compositions, compounds, or macromolecules which inhibit Notch signaling. Suitable Notch signaling inhibitors include, but are not limited to, antibodies, peptides, proteins, small molecules, nucleic acids such as siRNA, or any combination thereof.

In some embodiments, the Notch signaling inhibitor is a gamma-secretase pathway inhibitor. The gamma-secretase pathway inhibitor may comprise a dipeptide class gamma-secretase pathway inhibitor, a sulfonamide class gamma-secretase inhibitor, a transition state mimic class gamma-secretase inhibitor, a benzodiazepine class gamma-secretase inhibitor, a benzocaprolactam class gamma-secretase inhibitor, or combinations thereof. In some embodiments, the gamma-secretase pathway inhibitor can comprise DAPT (N—[N-(3,5-Difluorophenacetyl-L-alanyl)]-S-phenylglycine t-butyl ester), 1-(S)-endo-N-(1,3,3)-Trimethylbicyclo[2.2.1]hept-2-yl)-4-fluorophenyl sulfonamide, WPE-III31C, S-3-[N'-(3,5-difluorophenyl-alpha-hydroxyacetyl)-L-alanilyl]amino-2,3-dihydro-1-methyl-5-phenyl-1H-1,4-benzodiazepin-2-one, (N)—[(S)-2-hydroxy-3-methyl-butyryl]-1-(L-alaninyl)-(S)-1-amino-3-methyl-4,5,6,7-tetrahydro-2H-3-benzazepin-2-one, or combinations thereof.

In some embodiments, the Notch signaling inhibitor comprises DAPT (N—N-(3,5-Difluorophenacetyl-L-alanyl)-S-phenylglycine t-butyl ester). DAPT is a gamma-secretase inhibitor and inhibits proteolytic cleavage of Notch to NICD, which is the transcription factor responsible for translocating into the nucleus and turning on gene expression.

In some embodiments, the Notch inhibitor can comprise a RBP-Jκ inhibitor. Inhibitors of RBP-Jκ may be identified using methods known to one of ordinary skill in the art. For example, medicinal and combinatorial chemistry methods well known to those skilled in the art can be used to modify known RBP-Jκ antagonists to form new RBP-Jκ inhibitors with improved efficacy for the purposes of the present invention. Recent work identified a small molecule that can inhibit the Notch transcriptional complex (ternary complex that includes RBPJ) (Astudillo et al., *Cancer Res.*, 2016, 76(12):3593-603).

Additional inhibitors of the gamma-secretase pathway can be identified by methods known in the art. For example, medicinal and combinatorial chemistry methods well known to those skilled in the art can be used to modify known PS-1 antagonists to form new gamma-secretase inhibitors with improved efficacy for the purposes of the present disclosure. Known gamma-secretase inhibitors rely on the known role of the gamma-secretase pathway, making some inhibitors more and some inhibitors less effective at influencing bone growth. Accordingly, known factors may also be evaluated for their ability to create the results desired for the novel application disclosed herein.

The Notch signaling inhibitor may alter Notch signaling activity either directly or indirectly. For example, the Notch signaling inhibitor may block ligand binding to Notch receptors or alternatively, may block protein-protein binding activities occurring downstream of Notch receptor activation. Such inhibitors may provide the basis of therapeutics by their inherent properties. Indirect modulation of Notch signaling can occur at any step of the NICD cleavage and release process including at the nucleic acid level, transcriptional level, translational level, protein-folding level, and enzymatic cleavage level.

The one or more cells can be any cell type generally known to produce cilia and in which expresses a portion or all of the components of a Notch signaling pathway. The one or more cells are generally known to produce motile cilia. The one or more cells can have cilia which are reduced in amount or function, or are otherwise deficient or compromised in typical features such as ciliary length due to disease, environmental-induced damage, genetic mutation, or other factor(s). In some embodiments, the one or more cells may have little to no cilia or, if cilia present, little to no cilia having adequate functionality, as compared to wild-type cells of the same cell type. In some embodiments, the one or more cells are epithelial cells. In some embodiments, the epithelial cell is an airway epithelial cells. In some embodiments, the one or more cells are glial cells. In some embodiments, the glial cell is an ependymal cell. In some embodiments, the one or more cells are renal cells.

The subject can be can be any mammalian subject, for example a human, dog, cow, horse, mouse, rabbit, etc. In some embodiments, the subject is a primate. In some embodiments, the primate is a human. The subject can be a male or female of any age, race, creed, ethnicity, socio-economic status, or other general classifiers.

Environmental insults, genetic mutations, and/or aging can reduce or compromise cilia and ciliary function. In some embodiments, the subject has a disease, for example, a ciliopathy. A ciliopathy is a disease caused by genetic mutation, manifesting as reduced ciliation or dysregulated, defective, or dysfunctional cilia. Examples of ciliopathies include Primary Ciliary Dyskinesia (PCD), Bardet-Biedl syndrome (BBS), hydrocephalus, Joubert syndrome, Meckel syndrome, and Marden-Walker syndrome. In some embodiments, the subject has a disease caused by environmentally-induced damage, for example due to exposure to toxic compounds. For example, exposure to cigarette smoke, coal ash, industrial dust and fumes, poorly ventilated cooking/culinary fumes or fireplace/furnace fumes can cause chronic bronchitis and emphysema, or further lead to Chronic Obstructive Pulmonary Disease (COPD). In some embodiments, administration of the Notch signaling inhibitor treats a disease of the subject.

In some embodiments, the subject has a respiratory disease or a degenerative lung disease. Pulmonary motile cilia can exhibit rhythmic waving or beating motions, often quantifiable as ciliary beat function, which helps to propel mucous and fluids along mucosal surfaces, thereby facilitating the removal of microbes and particles from the lungs and respiratory tract. Accordingly, defects in pulmonary cilia can cause infection by respiratory pathogens, inflammation (e.g., bronchitis), cancer, or a host of other pulmonary pathologies. In some embodiments, the subject has Chronic Obstructive Pulmonary Disease (COPD), Emphysema, Asthma, Primary Ciliary Dyskinesia (PCD) or Cystic Fibrosis (CF). In such embodiments, the one or more cells typically are epithelial cells, particularly airway epithelial cells.

Without wishing to be bound by any one particular theory, in some embodiments, a Notch signaling inhibitor can improve lung clearance by pushing the cellular phenotype from a mesenchymal to epithelial transition and differentiating cells into healthy ciliated ones. In addition, differentiating lung epithelial cells into a committed ciliated cell type can reduce the number of multipotent cells following the goblet cell pathway, hence reducing the number of cells producing mucin. Such enhanced clearance protects lungs from ongoing environmental insults in diverse diseases ranging from allergy-associated asthma to on-going damage in COPD. Enhanced clearance also benefits patients with PCD and CF where compromised lung clearance leads to life-long pulmonary insults, development of bronchiectasis and eventual need for lung transplantation.

In some embodiments, the subject has a disease affecting the nervous system, particularly a disease affecting flow of the cerebrospinal fluid (CSF). Ventricular cilia can exhibit similar wave-like motions as pulmonary motile cilia, thereby facilitating circulation of CSF in the ventricular system. Defects in ventricular cilia can cause accumulation of CSF, particularly in the brain, thereby causing hydrocephalus. Accumulated CSF can increase pressure in the brain, leading to symptoms such as headache, double vision, poor balance, urinary incontinence, personality change, mental impairment, increase in head size, vomiting, sleepiness, seizures, downward pointing of the eyes, etc. In some embodiments, the subject has hydrocephalus. In such embodiments, the one or more cells typically are glial cells, particularly ependymal cells, more particularly ventricular ependymal cells.

In some embodiments, the subject has a disease affecting the renal system. In some embodiments, the disease comprises polycystic kidney disease.

Modification of ciliogenesis, or modifying ciliogenesis, as used herein, refers to a desirable change in number, functionality, productiveness, or characteristics of cilia. In some embodiments, modification of ciliogenesis may result in the disruption (e.g., dismantling) of cilia prior to occurrence of a desirable change. For instance, ciliogenesis is often correlated with the cell cycle, whereby cilia are dismantled and disappear prior to mitosis, then reappear thereafter. Thus, in some embodiments, the modification can first result in an undesirable change (e.g., reduction in ciliation), followed by an ultimately overall desirable change (e.g., subsequent and overall increase in ciliation).

In some embodiments, the modification of ciliogenesis can result in an increase in the number of cilia on the one or more cells. An increase in the number of cilia is also referred to herein as an increase in ciliation, an increase in percent (or percentage) ciliation, or an increase in cilia. An increase in the number of cilia can be determined by, for example, an increase in the total number or average number of cilia per cell. In some embodiments, the increase in the number of cilia can be determined by direct methods (e.g., visualization of cilia by microscopy), or alternatively by indirect methods, for example by an increase in signal representing cilia per cell (e.g., immunofluorescence, Western blot, etc.). In some embodiments, the increase in ciliation can be measured by qPCR of genes encoding structural proteins of the cilia or the basal body of the cilia.

A modification of ciliogenesis resulting in an increase in the number of cilia on the one or more cells includes an increase which is statistically significant. In some embodiments, the increase in the number of cilia on the one or more cells is by at least 10% compared to a control. In some embodiments, the increase in the number of cilia on the one or more cells is by at least 20%, at least 25%, at least 30%, at least 40%, at least 50%, at least 75%, at least 100%, at least 150%, at least 200%, at least 250%, or at least 300%, as compared to a control.

In some embodiments, the modification of ciliogenesis can result in an increase in length of cilia on the one or more cells. Increased ciliary length can increase fluid flow by virtue of longer sweeping motions. An increase in the length of cilia can be determined by, for example, an increase in the average length of cilia per cell. In some embodiments, the increase in the number of cilia can be determined by direct methods (e.g., visualization of cilia by microscopy), or alternatively by indirect methods, for example by an increase in signal representing cilia per cell (e.g., immunofluorescence, Western blot, etc.). In some embodiments, an increase in length of cilia can be measured by qPCR of genes encoding structural proteins of the cilia or the basal body of the cilia.

A modification of ciliogenesis resulting in an increase in the length of cilia on the one or more cells includes an increase which is statistically significant. In some embodiments, the increase in the length of cilia on the one or more cells is by at least 10% compared to a control. In some embodiments, the increase in the length of cilia on the one or more cells is by at least 15%, at least 20%, at least 25%, at least 30%, at least 40%, at least 50%, at least 75%, at least 100%, at least 150%, at least 200%, at least 250%, or at least 300%, as compared to a control.

In some embodiments, the modification of ciliogenesis can result in an increase in cilia beat frequency on the one or more cells. Cilia beat frequency is also referred to herein as ciliary beat frequency or CBF. Cilia can move or "beat" to produce coordinated, metachronal waves to generate directional fluid flow. Increased cilia beat frequency can increase fluid flow rates. An increase in cilia beat frequency can be determined by, for example, an increase in the average ciliary beats per unit of time per cell. In some embodiments, the increase in cilia beat frequency can be determined by direct methods (e.g., visualization of cilia motion by video-microscopy). Alternatively, increased cilia beat frequency can be determined by indirect or functional methods, for example by an increase in fluid flow across the cell or cells, as measured by an increase in fluid flow rate or flow volume, or other fluidics metrics, such as using small beads in the culture medium and tracking the rate of their movement across the ciliated cell surface.

A modification of ciliogenesis resulting in an increase in the cilia beat frequency of the one or more cells includes an increase which is statistically significant. In some embodiments, the increase in the cilia beat frequency of the one or more cells is by at least 5% compared to a control. In some embodiments, the increase in the cilia beat frequency of the one or more cells is by at least 10%, at least 15%, at least 20%, at least 25%, at least 30%, at least 40%, at least 50%, at least 75%, at least 100%, at least 150%, at least 200%, at least 250%, or at least 300%, as compared to a control.

A modification of ciliogenesis can be determined by an array of methods. For example, a modification be examined on a cell, a representative portion of a cell, multiple cells, a representative portion of two or more cells, tissues, organs, or in a subject or group of subjects. Because of the large number and small size of cilia relative to a cell bearing those cilia, examination of cilia can, in some embodiments, be performed by observing one or more portions of the cell (e.g., by microscopy, wherein various fields of view are of various portions of the same cell). Alternatively, a modification of ciliogenesis on one or more portions of a first cell can be observed and measured, and combined with or compared to similar measurements made on one or more portions of a second cell. In some embodiments, the results of each observation can be averaged together or, alternatively, summed together, and compared to a control. In some embodiments, the one or more cells of a subject comprises a multitude of cells of a subject, and wherein the increase in the number of cilia, the increase in the length of cilia, and/or the increase in the beat frequency of cilia is determined based on an average obtained from the multitude of cells of a subject.

A modification of ciliogenesis is compared to a control. Because a given ciliated cell type can contain cilia which typically have different characteristics or properties (e.g., shorter length) than cilia of another cell type, a change in those characteristics or properties is typically measured in comparison to the same cell (e.g., before and after treatment of the same cell) or in comparison to the same or similar cell type (e.g., a first sample of airway epithelial cells are analyzed before treatment, and a second sample of airway epithelial cells are analyzed after treatment). Thus, in some embodiments, a control can be the same cell or a second cell of the same or similar cell type. Generally, the one or more cells of the subject and the control cell are both from the same general anatomical region (e.g., both are epithelial cells isolated from a trachea). The control can be a biological sample from the same subject from which the one or more cells are obtained. Alternatively, a collection of values used as a standard applied to one or more subjects (e.g., a general number or average that is known and not identified in the method using a sample) can be used as a control.

The modification of ciliogenesis can result in observable changes occurring in short (e.g., hours) or longer (e.g., days) periods of time. Numerous factors can affect the rate at which a result of modification of ciliogenesis can be observed or measured, including the cell type, dosage and route of administration of Notch signaling inhibitor, degree or severity of disease or condition, and the type of result sought to effectuate from the modification of ciliogenesis. In some embodiments, the result of modification of ciliogenesis (e.g., the increase in the number of cilia, the increase in the length of cilia, and/or the increase in the beat frequency of cilia) is achieved in ten days or less. In some embodiments, the result of modification of ciliogenesis is achieved in nine days or less, eight days or less, or seven days or less. In some embodiments, the result of modification of ciliogenesis is achieved within seven to ten days, or within seven to nine days. The time frame from which a result of modification of ciliogenesis is achieved begins at the time in which the Notch signaling inhibitor is administered to the subject, and ends when the result of the modification of ciliogenesis is substantially unchanged thereafter.

Included herein are methods comprising administering to a subject an effective amount of a composition comprising a Notch signaling inhibitor. The term "effective amount" of an agent refers to a sufficient amount of a Notch signaling inhibitor to provide a desired effect. The desired effect can be in a cell or portion thereof, plurality of cells, tissue, organ, or subject. In some embodiments, the desired effect is modulation of ciliogenesis and thus, an effective amount of a Notch signaling inhibitor is an amount sufficient to result in modulation of ciliogenesis, for example increased ciliation, increased cilia length, and/or increased cilia beat frequency.

In some embodiments, the amount of a composition comprising a Notch signaling inhibitor administered is an amount sufficient to treat a disease (e.g., a therapeutically effective amount). A "therapeutically effective amount" or "therapeutically effective dose" of a composition (e.g. a composition comprising an agent) refers to an amount that is effective to achieve a desired therapeutic result. Thus, the terms "therapeutically effective amount" or "therapeutically effective dose" refer to an amount of a Notch signaling inhibitor that will elicit in a subject the biological or medical response of a cell, tissue, system, animal, or human that is being sought by the researcher, veterinarian, medical doctor or other clinician. In some embodiments, a therapeutically effective amount of a Notch signaling inhibitor is administered to a subject to result in increased ciliation, increased cilia length, and/or increased cilia beat frequency to a level sufficient to treat a disease. In some embodiments, the therapeutically effective amount of a Notch signaling inhibitor administered to a subject results in increased productivity of cough; increased mucous flow; reduced pulmonary inflammation/bronchitis; reduced coughing, wheezing, chest tightness, chest pain, and/or shortness of breath; reduced microbial infection or reduced occurrence thereof; reduced cyanosis; normalization of mucous color; subject weight stabilization; reduced emphysema; reduced severity or frequency of asthma attacks; reduced need for use of a rescue inhaler; reduced severity or frequency of ear, nose, or throat infections; reduced nasal congestion; increased tolerance of exercise/physical exertion; reduced constipation; normalization of stool; or any combination thereof. In some embodiments, a therapeutically effective amount of a Notch signaling inhibitor is administered to a subject to result in reduced water/CSF retention in the brain; reduced severity or frequency of headache, vomiting, irritability, seizure, and/or double vision; improved muscle coordination, flexibility, tone, and/or responsiveness; improved energy level, focus, cognition, and/or appetite; normalization of sleep schedule; or any combination thereof.

A therapeutically effective amount of a Notch signaling inhibitor that will elicit in a subject the desired biological or medical response can be demonstrated in the subject as a whole (e.g., by clinical evaluation of the subject), or in a sample obtained from the subject (e.g., a tissue or cell sample). In some embodiments, a cell can be analyzed. In such embodiments, a sample of the cell (e.g., a sufficient portion of the cell surface) or a number of cilia can be analyzed for characteristics or function which are representative of the cell overall. In some embodiments, two or more cells (e.g., a plurality of cells) can be analyzed. In such embodiments, a sample of the two or more cells (e.g., a sufficient number of the two or more cells) cells and/or a sample of each cell selected (e.g., a sufficient portion of the cell surface of each selected cell) can be analyzed for characteristics or function which are representative of the two or more cells overall. A sample is representative of the larger whole when there is a statistical likelihood that the remaining portions of the whole would be statistically similar to the measured portion.

Dosages are typically modified according to the characteristics of the subject (weight, gender, age, etc.), severity of disease (e.g., degree of reduced ciliation), specifics and purity of the Notch signaling inhibitor to be administered, route of administration, nature of the formulation, and numerous other factors. Generally, the Notch signaling inhibitor is administered to the subject at a dosage ranging from 0.1 µg/kg body weight to 100 g/kg body weight. In some embodiments, the Notch signaling inhibitor is administered to the subject at a dosage of from 1 µg/kg to 10 g/kg, from 10 µg/kg to 1 g/kg, from 10 µg/kg to 500 mg/kg, from 10 µg/kg to 100 mg/kg, from 10 µg/kg to 10 mg/kg, from 10 µg/kg to 1 mg/kg, from 10 µg/kg to 500 µg/kg, or from 10 µg/kg to 100 µg/kg body weight. Dosages above or below the range cited above may be administered to the individual patient if desired.

The Notch signaling inhibitor can be administered by any herein disclosed method of administration. The method can include systemic administration (e.g., by oral or intravenous delivery), local administration, or combination thereof. In some embodiments, the Notch signaling inhibitor can be administered inhalationally. Inhalational administration can deliver the Notch signaling inhibitor to airway epithelial cells, particularly airway epithelial cells in need of modulation of ciliogenesis. Suitable devices for inhalational administration include, for example, an inhaler, nebulizer, vaporizer, or other equipment suitable for producing an inhalant. In some embodiments, the Notch signaling inhibitor can be administered intrathecally. Intrathecal administration can deliver the Notch signaling inhibitor to the ependyma, particularly cerebrospinal ependymal cells in need of modulation of ciliogenesis. Suitable devices for intrathecal administration include, for example, an injection syringe, intrathecal pump, or other equipment suitable for intrathecal administration.

The administering step can include at least one, at least two, at least three, at least four, at least five, at least six, at least seven, at least eight, at least nine, or at least ten dosages. In some embodiments, the administering step can include one or more dosages as needed. The administering step can be performed before the subject exhibits disease symptoms (e.g., prophylactically), or during or after disease symptoms occur. The administering step can be performed prior to, concurrent with, or subsequent to administration of other agents to the subject. In some embodiments, the administering step is performed prior to, concurrent with, or subsequent to the administration of one or more additional diagnostic or therapeutic agents.

The present disclosure further contemplates derivatives and analogs of each Notch signaling inhibitor disclosed herein. Derivatives and analogues of a compound include, but are not limited to, any salts, esters, acids, bases, solvates, hydrates, prodrugs, etc. Derivatives, modifications, and pharmaceutically acceptable salts retain the functional properties described herein.

In some embodiments, the method can further include administering to the subject a therapeutically effective amount of a Notch signaling inhibitor, or derivative thereof, and a pharmaceutically acceptable excipient. Suitable excipients include, but are not limited to, salts, diluents, binders, fillers, solubilizers, disintegrants, preservatives, sorbents, and other components. Also disclosed herein is a medicament comprising a pharmaceutically effective amount of a Notch signaling inhibitor, or derivative thereof.

The methods disclosed herein can, in some embodiments, affect gene expression, particularly expression of genes involved in or related to ciliogenesis. In some embodiments, the methods increase expression of genes related to constructing, lengthening, thickening, and/or functionalizing cilia. In some embodiments, the methods decrease expression of genes related to deconstructing, removing, decreasing size/thickness, and/or defunctionalizing cilia. In some embodiments, the methods alter the expression of Hes1, Hes5, Hey1, Notch1, Psen1, Hif1α, nNOS, iNOS, eNOS, or any combination thereof. In some embodiments, the alteration of gene expression results in treatment of a disease.

1. Optionally, the Notch signaling inhibitor, or derivative thereof, can be formulated in a medicament. The Notch signaling inhibitor, or derivative thereof, can be formulated in any suitable medicament including, for example, but not limited to, solids, semi-solids, liquids, and gaseous (inhalant) dosage forms, such as tablets, pills, powders, liquid solutions or suspensions, suppositories, injectables, infusions, inhalants, hydrogels, topical gels, sprays, and the like. Optionally, the medicament comprises a pharmaceutically acceptable excipient and/or suitable diluent. Typically, the medicament comprises an effective or pharmaceutically effective dose of the Notch signaling inhibitor. Accordingly, included herein are medicaments for modifying ciliogenesis in one or more cells of a subject, comprising a pharmaceutically effective amount of a composition comprising a Notch signaling inhibitor, wherein the modification results in an increase in a number of cilia, an increase in a length of cilia, and/or an increase in a beat frequency of cilia as compared to a control. The Notch signaling inhibitor can be any as described herein. Also included herein are medicaments for modifying ciliogenesis in one or more cells of a subject, comprising a dosage form of Notch signaling inhibitor from 0.1 µg to 100 g/kg of the subject.

Methods of Detecting Ciliogenesis

Provided herein is a facile model of reciliating mouse tracheal cells in vitro in a controlled fashion, facilitating the study of ciliogenesis and the role of various genes involved. The disclosed protocol is highly reproducible, leading to successful reciliation in over 90% of trials, and is completed in a shortened time of about 2 weeks. Pronase digestion facilitates recovery of a desirable number of viable tracheal epithelial cells, and thus reduces the number of animals needed per treatment/study group (one trachea per well of a 6-well plate, 2-3 wells/suspension flask). Since only one trachea was required per well, the number of animals necessary for euthanasia was reduced. Reduced requirements for animals is particularly useful in studying animal models of disease where transgenic mouse models may be more expensive or have reduced fertility or reduced viability, making the generation of adequate number of animals for study an issue of considerable practical importance. In addition, reducing the number of animals for experimentation is a stated goal of all institutional animal use and care review committees. The disclosed protocol also has much simpler media requirements with only Ultroser-G or NuSerum needed for stationary media and suspension media, respectively (added to DMEM/F12 and antibiotic/antimycotic). This is in sharp contrast to the extensive media requirements of the air-liquid interface protocol, including multiple antibiotics, antifungals, growth factors and vitamins, thereby adding to the complexity and expense of the air-liquid interface protocol (Karp, et al., *Methods Mol. Biol.*, 2002, 188:115-137; You, et al., *Am. J. Physiol. Lung Cell Mol. Physiol.*, 2002, 283:L1315-1321). The herein disclosed protocol yields a relatively homogenous population of ciliated epithelial cells with little to no generation of mucous or basal cells.

Also disclosed is a method to quantitate degree of reciliation (percentage reciliation) using freely available programs (ImageJ, Fiji). Macros and detailed methodology for automated calculation of cilia length and cilia beat frequency are also presented herein. All three cilia-related variables were significantly enhanced by low dose DAPT at 2 nM concentrations. These effects were observed in mouse tracheal epithelial cells and human nasal epithelial cells to a very similar extent. In addition, the protocol lends itself to siRNA knockdown to assess roles of different genes in ciliogenesis. The feasibility of the disclosed approach is demonstrated herein by knocking down Dnai1, an essential component of cilia microtubules, mutations of which are a known cause of PCD (Shapiro, et al., *Pediatr. Pulmonol.*, 2016, 51:115-132). Indeed, Dnai1 knockdown was associated with markedly inhibited ciliogenesis, with only rare cilia forming that were almost immotile.

In addition to reciliating epithelial cells, the disclosed protocol can be used to study reciliation of human nasal epithelial cells in a similarly facile and efficient manner. Because the number of cells obtained from scraping the inferior turbinate yields fewer cells than those obtained from an entire mouse trachea, the days in stationary culture needed to reach confluence ranges from about 2-4 weeks. However, once in suspension, reciliation is again achieved in about 8 days. Similar to mouse data, reciliation of human nasal epithelial tissue was significantly enhanced with 2 nM DAPT, with significant increases in cilia length and cilia beat frequency.

In summary, disclosed herein is a protocol for efficiently reciliating mouse tracheal epithelial cells in about 2 weeks with over 90% success rates. With minor modifications, the protocol can be applied to human nasal epithelial tissue as well. This protocol can be used to study influence of various genes on ciliogenesis and to test small molecule inhibitors or stimulators of key transcriptional factors to study their role in ciliogenesis in a hypothesis driven manner.

A number of embodiments of the invention have been described. Nevertheless, it will be understood that various modifications may be made without departing from the spirit and scope of the invention.

EXAMPLES

To further illustrate the principles of the present disclosure, the following examples are put forth so as to provide those of ordinary skill in the art with a complete disclosure and description of how the compositions and methods claimed herein are made and evaluated. They are intended to be purely for purposes of example and are not intended to limit the scope of the disclosure. These examples do not exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1: Rapid Ex-Vivo Reciliation of Human and Murine Respiratory Epithelia for Functional Assessment of Ciliogenesis and Motile Cilia Function Abstract The respiratory epithelia have motile cilia that play an essential role in airway clearance. Defects in motile cilia function can cause severe sinopulmonary disease such as in primary ciliary dyskinesia (PCD). Disclosed herein is a simple, rapid ex vivo reciliation protocol for generating motile ciliated respiratory airway epithelia from mouse trachea. The protocol facilitates investigations into cilia defects associated with airway diseases. The protocol includes the isolation of mouse trachea epithelia for monolayer culture, then about 7-10 days of proliferative growth, followed by suspension culture to stimulate robust de novo ciliogenesis. Motile cilia were visible at about 5 days, with ciliogenesis largely complete by about 7-9 days. This same protocol is used to reciliate nasal epithelial cells obtained from the inferior nasal turbinate of human subjects, including patients with various ciliopathies. This ex vivo culture method was also used to assay genes and small molecules for their efficacy in modulating ciliogenesis. siRNA knockdown of Dnai1, a cilia outer dynein arm component associated with PCD, resulted in immotile cilia similar to that seen in PCD patients. Further, cell treatments with a small molecule inhibitor of Notch signaling (DAPT) enhanced production of ciliated airway epithelia, with the cilia generated being significantly longer and faster beating. Thus, DAPT can be used for therapeutic intervention in various airway diseases, for example to stimulate ciliogenesis. Large-scale screens of small molecules can be conducted using ex vivo culture of respiratory epithelia from mutant mouse models to identify novel therapeutic compounds for the treatment of respiratory diseases.

Methods

Mouse Trachea Isolation:

All animal protocols were approved by the University of Pittsburgh Animal Care and Use Committee. Wild-type, C57B6, adult mice (6-8 weeks of age) were euthanized with inhalational $CO_2$, anterior neck regions were washed with 70% ethanol, and a transverse incision was made across the neck at the mid-cervical level. Skin and subcutaneous tissue were dissected out, revealing the sternocleidomastoid muscles that were incised across and pulled over to reveal the trachea, easily identified as a ringed structure. The trachea was gently dissected from the underlying adherent esophagus and connective tissue, pulled out and transected proximally first from the larynx and then distally as far down as possible, close to the carina, and placed in a petri dish containing about 10 ml Leibovitz-15 solution (Gibco; 21083). Isolated tracheas were cleaned of adherent muscle tissue, blood vessels and fat under a dissecting microscope, then incised, splaying the trachea length-wise.

Pronase Digestion:

Twelve ml of Leibovitz-15 solution were placed in a 15 ml falcon tube, and 6 cleaned, incised tracheas were added to each tube. Pronase (Protease from *Streptomyces griseus*, Sigma, P5147) was added to a final concentration of 1.5 mg/ml (Stock solution, 150 mg/ml, 100×) and placed in 4° C. overnight with gentle shaking. After incubation, Pronase was neutralized with addition of fetal bovine serum to a final concentration of 10% (1.2 ml/tube). Tracheas and denuded epithelial cells were centrifuged at 1200 rpms for 6 minutes. Supernatant was aspirated, and trachea/cells were re-suspended in 12 ml Stationary media (500 ml DMEM/F12, 10 ml of Ultroser G, and 10 ml of 100× Antibiotics-Antimycotic). The cells/tracheas were pipetted up and down vigorously 12-20 times, and vortexed to re-suspend pelleted tracheas if necessary. Trachea/cells were centrifuged again, supernatants were aspirated, pellets were re-suspended in 6 ml of stationary medium, and then everything was transferred to a Primaria plate (Corning, 353803) or a regular cell culture plate (Corning, 353003), and incubated at 37° C./5% $CO_2$ for 6 hours. This was performed to plate out fibroblasts, thereby minimizing contamination of tracheal epithelial cells with fibroblasts. After incubation, non-adherent cells were collected by lightly washing the plates with stationary media present in the plates. Cells were pelleted, supernatant aspirated, cells re-suspended in 12 ml of stationary medium and added to a 6-well plate (2 ml/well) coated with rat tail collagen.

Human Nasal Epithelia Isolation:

Cells were obtained by scraping the inferior nasal turbinate using a rhinoprobe under direct visualization from human subjects with congenital heart defects as well as healthy human volunteers. Cells were immediately placed into 5 ml Leibovitz-15 medium prior to processing for stationary culture.

Stationary Culture:

Tracheal epithelial cells were obtained from mice and processed for stationary culture as detailed above. The tracheal epithelial cells were placed onto rat-tail collagen coated wells and then incubated at 37° C./5% $CO_2$ for 36-48 hrs. Over the course of about 48 hours, the cells seeded onto the collagen lost their cilia and underwent proliferative growth, expanding in numbers. By 48 hrs, large islands of cells were established and grew rapidly, reaching confluence by about 7-10 days (FIGS. 1A-1F). Cells were fed with stationary media every 2 days following the initial seeding.

Human nasal epithelial cells were obtained by gently scraping the inferior turbinate using a rhinoprobe under direct visualization and placed into 5 ml of Leibovitz-15 medium. These cells were spun down, the supernatant was aspirated, cells were resuspended in 6 ml of stationary medium, and then plated onto 3 wells of a 6-well rat tail collagen coated plate. The media was changed 48-72 hours post plating and fed every 2 days until confluence was reached. Following confluence, the treatment of mouse tracheal epithelial cells and human nasal epithelial cells was identical e.g., placement into suspension culture, video microscopy, etc. siRNA knockdown was only performed in mouse tracheal tissue due to the paucity of human nasal epithelial cells.

Suspension Culture:

Once confluence was reached, typically occurring between about 7 to 10 days, the stationary media was aspirated, and collagen was digested with 1 ml of Collagenase 4 (200 IU/ml, Worthington, LS004210) for 75-90 mins at 37° C./5% $CO_2$. After incubation, collagenase was neutralized using 2 ml of Suspension media (500 ml DMEN/F12, 50 ml NuSerum, 10 ml 100× Antibiotics-Antimycotic). Cells adherent to the bottom of the plate were gently scrapped off with a cell scraper (Fisherbrand, 08-100-241). The contents of three wells were transferred to a 15 ml falcon tube, and cells were centrifuged at 1200 rpm for 6 minutes. Pelleted cells were washed twice with 12 ml Suspension media, resuspended in 12 ml Suspension media, and placed in a T-25 flask with a non-rebreathing top. A non-rebreathing flask cap is important, as a filter top interferes with ciliogenesis. Ciliogenesis in vitro is dependent on activation of Hif-1α transcription factor, which is activated by relative hypoxia in an air-liquid interface culture (Ito, et al., *Am. J. Respir. Cell Mol. Biol.*, 2011, 45:938-945). The T-25 flasks were positioned such that the necks were upwardly inclined by about 10-20 degrees to prevent cells from sludging in the neck region, and were placed on an orbital shaker at 80 rpms, 37° C. Conditions were maintained for about 7-10 days without any change of the suspension medium. Small, non-motile cilia appeared by day 5 to 6, with ciliogenesis complete typically by about days 7-9. Motile cilia were easily identified and imaged typically on Day 8.

Figure 2B:
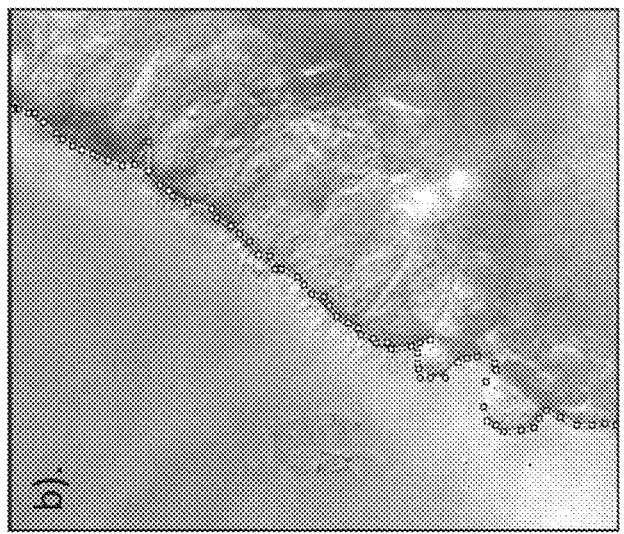
FIG. 2B: The surface of spheroids that could potentially contain cilia (e.g., reciliate) was outlined. The outlined portions were visible in a video and represent a sheet of cells reciliated on the cell surfaces facing the lumen of the trachea. Hence, only one ciliated face of a three-dimensional cuboidal-shaped cell was outlined. A thin line showing small white dots at each vertex of the hand-drawn line was sketched along the spheroid surface. The ImageJ program calculated the length of the sketched line.
Figure 2C:
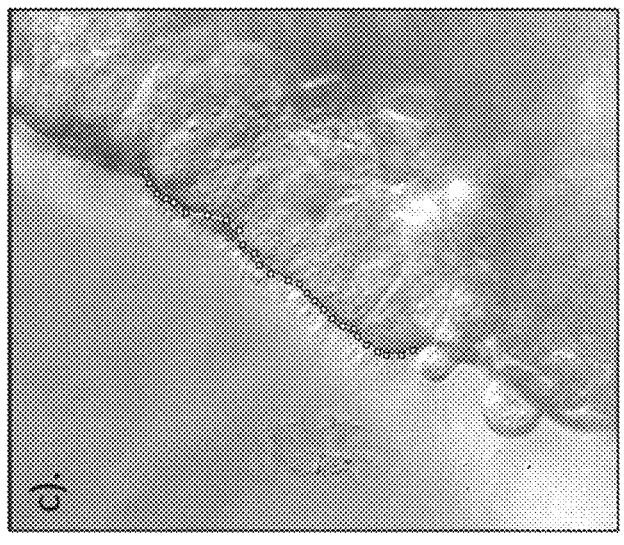
FIG. 2C: The surfaces of spheroids that actually contained cilia were outlined, thereby excluding the unciliated zones on the spheroid surface. Dividing the total reciliated surface zones by the total spheroidal surface provided percent reciliation.

Assessing Ciliogenesis:

Reciliation was observed by about days 7 to 9 with high-speed video-microscopy (200 fps) with a 60× oil-immersion lens (FIG. 2A). Imaging was performed typically on day 8 of suspension culture. Care was taken to avoid translational motion or changes in focal plane during video acquisition. Imaging was optimized by taking profile views of reciliated tissue. This allowed for more accurate measurements of ciliary beat frequency and motion, and more accurate assessments of degree of reciliation. Cines videos were converted into .avi format and imported into ImageJ program. FIG. 2 shows cells integrated in a tissue that was generated by reciliation. The entire perimeter of the tissue surface which had cilia or had the potential to grow cilia was outlined using a free-hand line drawing tool (FIG. 2B). Additionally, only the ciliated perimeter of the cell surface in each micrograph was outlined (FIG. 2C). The outlined total surface and ciliated surface alone was quantified. Extent of ciliation was calculated by dividing the length of ciliated surface by the length of the entire surface available for ciliation, and converted to a percentage.

To measure cilia length in reciliated nasal tissue, each recording was processed with a custom script written for Fiji, an open-source image analysis software (Schindelin, et al., *Nat. Methods*, 2012, 9:676-682). This script used the Temporal Median filter to segment patches of cilia based on movement, and the Thickness tool in the BoneJ analysis toolkit (Doube, et al., *Bone*, 2010, 47:1076-1079) measured average cilia length. Ciliary beat frequency was measured in cilia beats per second (Hertz).]

Human Nasal Epithelial Reciliation:

Nasal epithelial cells were cultured using a modification of the above protocol. All human protocols were approved by University of Pittsburgh Institutional Review Board. After informed consent, cells were obtained from scraping the inferior nasal turbinate using a rhinoprobe under direct visualization from subjects with congenital heart defects, and immediately placed into 5 ml of Leibovitz-15 medium. After video-microscopy of the initial scrape was performed and presence of ciliated cells confirmed, cells were centrifuged at 1200 rpm for 6 minutes. Supernatant was aspirated, cells were resuspended in 2 ml stationary media, and plated onto 3 rat tail collagen coated wells of a 6-well plate. Cells were grown to confluence, collagen was removed by collagenase treatment, and cells were placed into suspension culture as per the protocol above. Similar to mouse tracheal cells, reciliation occurred by about 5-6 days, and was complete by about 7-9 days. Imaging was typically performed on day 8 post-placement into suspension culture.

Figure 3:
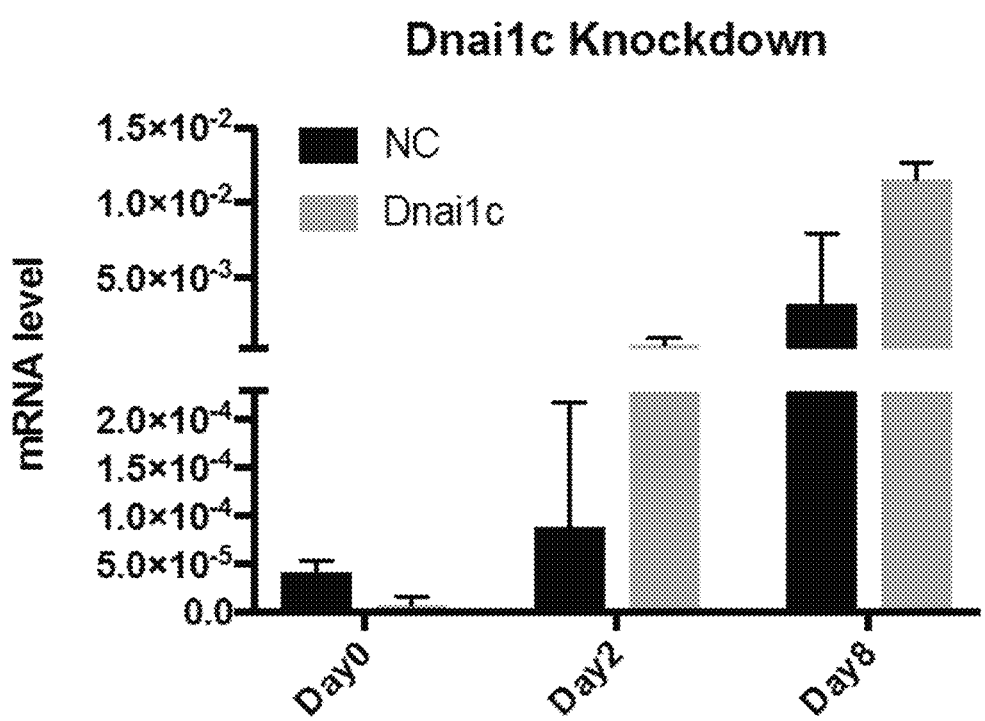
FIG. 3 is a graph showing knockdown of Dnai 1c by siRNA in mouse tracheal epithelial cells. Significant reduction in expression of Dnai 1c was achieved as compared to control, scrambled siRNA (NC). Dnai 1c knockdown was apparent immediately post-knockdown (within 6 hours on Day 0). Rebound increase in expression occurred over the next 2 to 8 days. Expression of Dnai 1c was normalized to actin. This experiment validated the disclosed approach to effective reciliation by showing that knocking down an essential structural component of motile cilia leads to depression of ciliogenesis.

Ciliogenesis Knockdown:

The herein disclosed ciliogenesis protocol was used to test the role of genes in the complex process of ciliogenesis, demonstrating the feasibility of this approach. Upon reaching confluence, siRNA knockdown of the mouse airway epithelium was performed in stationary culture using the protocol detailed below prior to placing cells in suspension (FIG. 3). Stationary media was aspirated the day before knock down, cells were washed with 2 ml of antibiotic-free media, and cells were resuspended in 1.7 mL of antibiotic-free stationary medium (500 mL DMEM/F12, 10 mL of Ultroser G, no antibiotics) overnight. A cocktail of 4 siRNAs (Qiagen FlexiTube siRNA) designed to knockdown the gene of interest (2.5 µL of a 10 µM stock solution each) was added to 140 µL Opti-MEM (Life Technologies, 31985-062) to provide a total volume of 150 µL. A second mix of 7.5 µL of Lipofectamine RNAiMax (Invitrogen, 13778030) was added to 142.5 µL of Optimem. The siRNA cocktail/Opti-MEM mixture and Lipofectamine RNAimax/Opti-MEM mixture were incubated together for 5 min at room temperature, then added to each well containing confluent mouse tracheal epithelial cells to a 2 mL final well volume. Cells were incubated on a shaker at 37° C./5% $CO_2$ for 3 hours. After incubation, media was aspirated and replaced with 1 mL collagenase, and cells were placed into suspension per the "Suspension Culture" protocol. Scrambled siRNA transfection was used as a negative control in all siRNA knockdown experiments.

A sample of cells from the suspension culture was obtained on Day 0 (day of suspension), Day 2 and Day 8 post-transfection to assess knockdown efficiency. Cellular RNA was extracted using RNeasy Plus Micro Kit (Qiagen, 74134) and converted to cDNA using a High-Capacity RNA to cDNA Kit (ThermoFisher, 4387406). Two primer pairs were designed for each siRNA knockdown experiment to confirm extent of knockdown, and normalized relative to (3-actin expression in a real time PCR reaction.

Affecting Extent of Ciliogenesis Utilizing Small Molecules:

The protocol was used to assess the role of small molecule inhibitors or activators on ciliogenesis. A dose response effect on ciliogenesis of DAPT (N—[N-(3,5-Difluorophenacetyl)-L-alanyl]-S-phenylglycine t-butyl ester; Selleckchem, S2215), a gamma-secretase inhibitor, was performed. Mouse tracheal cells were harvested and grown to confluence in stationary media as detailed above. After reaching 80-90% confluence, cells were treated with collagenase (200 IU/ml, Worthington, LS004210), collected using a cell scraper, and resuspended in suspension media with identical volumes of DMSO (vehicle for DAPT) at varying concentrations of DAPT: 2 nM, 20 nM, 200 nM and 2 µM. Cells were incubated on an orbital shaker at 37° C., 80 rpm, for 8 days before imaging with high-speed video-microscopy. A minimum of 8 videos were obtained per sample.

Statistical Analyses:

Continuous variables were assessed for the normality of their distribution by employing the skewness and kurtosis normality test. Normally distributed data were compared using a Student's t-test. Non-normally distributed data were compared using a Wilcoxon-rank sum test. A two-tailed p-value of <0.05 was considered significant. All analyses were performed using Stata 12.1 (College Station, Tex.).

Rat Tail Collagen Extraction:

All protocols were approved by the University of Pittsburgh Institutional Care and Use Committee. Mature rats (8-9) weeks old or sentinel rats at the end of their studies were euthanized. Post euthanasia, tails were removed as close to the base as possible and stored at −80° C. until extraction (maximum 3 months). Frozen rat tails were thawed and treated with 70% ethanol. Skin was incised using a scalpel lengthwise, starting from the base and working to the tip in 4-6 quadrants. The tail base was held with a surgical clamp, while the skin was peeled away using a second surgical clamp, thereby completely denuding the tail. The distal end of the tail was held between two surgical clamps, approximately 1-2 inches apart and about 1 inch from the tip of the denuded tail. The left clamp was held steady while the distal clamp was rotated to twist the tail until broken. The broken end was peeled away under constant pressure from the right surgical clamp, thereby exposing collagen fibres of the rat tail tendon. The white collagen fibres were removed via surgical scissors as close to the rat tail as possible and allowed to drop in a petri dish filled with milli-Q water to maintain fibre hydration. Collagen fibres were weighed and placed in an Erlenmeyer-flask with 100 ml of 0.5 M acetic acid/g of fibre. The flask was stirred at 4° C. until fibres dissolved (2-5 days). The solution was then centrifuged at 4700 rpm, 4° C., for 4 hours. The pellet was discarded, supernatant volumes were recorded, and the supernatant was again stirred at 4° C. One-ninth of the estimated supernatant volume (e.g., 100 mL for 900 mL supernatant) of cold 25% NaCl in 0.5 M acetic acid solution was added dropwise to the flask. The solution was stirred at 4° C. for 24 hours. The solution was then centrifuged (4700 rpm, 4° C., 4 hours), the pellet discarded, the volume of the supernatant measured, and the supernatant again mixed with 25% NaCl in 0.5 M Acetic acid. This time, $⅛^{th}$ of the volume of the supernatant was added dropwise and stirred at 4° C. for 24 hours. Collagen fell out of solution in white clouds. The solution was again centrifuged (4700 rpm, 4° C., 4 hours), the supernatant discarded, and the white pellet(s) collected. The pellet was resuspended in about 50 mL 0.1 M acetic acid added for every 300 mL of initial suspension volume, and incubated overnight at 4° C. The resultant solution served as stock solution to be used for coating flasks, culture dishes etc.

Coating Culture Dishes with Collagen:

Stock solution was allowed to reach room temperature slowly. Stock solution was diluted about 6-fold with 0.1 M acetic acid to prepare a viscous working solution. One drop of 1% phenol red solution (in PBS) was added and incubated until air bubbles disappeared (about 10-30 mins).

In a cell culture hood, the collagen solution was pipetted into culture flasks (e.g., 3 ml/T25, 7 ml/T75, 1 ml/well of a 6-well plate). Flasks were gently shaken to coat the surface evenly. The solution was polymerized by adding 1-2 drops of concentrated ammoniac solution (17 M) onto the collagen surface. The solution was covered and incubated for 10 minutes until the collagen turned pink. 1-2 more drops of 17 M ammoniac solution were added, and the flasks/plates were incubated 30-60 min. Flasks were uprighted, and 0.9% saline solution were added (10 mL/T25, 35 mL/T75, 2 mL/well of a 6-well culture plate), and incubated 37° C./5% $CO_2$ for at least 60 min or overnight. Thereafter, plates were washed with 0.9% saline solution, incubator at 37° C., and saline was removed just prior to use in further experiments.

Obtaining Nasal Epithelial Cells for Culture/Reciliation:

Nasal ciliated epithelial cells were obtained by scraping the inferior nasal turbinate with a rhinoprobe under direct visualization with aid of a nasal speculum. For sedated and/or intubated patients, nasal scrapes were carried out on the un-instrumented naris, if possible. Rhinoprobe (Arlington Scientific, Catalog #SY-96-0905), a small, plastic curette was drawn gently over the inferior surface of the inferior nasal turbinate several times. Cells so obtained were shaken into 5 mL Leibovitz 15 medium and immediately processed (video-microscopy and/or placement into culture as per protocol).

Automated Measurement of Cilia Length Using an ImageJ Macro:

The macro for detecting cilia length was performed in two steps. First the time-consuming Temporal Median filter was applied to all movies in a batch. Second, a highlighted cilia-rich region was selected from the one or more regions identified in the first step. The program measured the average cilia length in this region. Cilia were sampled with high spatial resolution and at a high frame rate (200 FPS) for accurate measurement. Both macros were written in ImageJ macro language.

```
Macro step 1: process movies using Temporal filter:
//this macro requires that the Temporal Median plugin be installed.
files = getDirectory("Movies to process");
list = getFileList(files);
n = lengthOf(list);
count=0;
maskDir = files+"/masks/"
if(!File.exists(maskDir)) {
    File.makeDirectory(maskDir);
}
setBatchMode(true);
for(i=0;i<n;i++) {
    open(files+list[count]);
    name=getTitle( );
    run("Slice Keeper", "first=1 last=400 increment=6");
    run("Temporal Median", "5, 3.5");
    run("Despeckle", "stack");
    run("Z Project...", "projection=[Sum Slices]");
    run("Subtract Background...", "rolling=50");
    run("Gaussian Blur...", "sigma=3");
    setThreshold(3.68, 30);
    run("Make Binary");
    run("Erode");
    run("Erode");
    run("Erode");
    run("Erode");
    run("Erode");
    run("Dilate");
    run("Dilate");
    run("Dilate");
    run("Dilate");
    run("Dilate");
    maskName = getTitle( );
    run("Add Slice");
    selectWindow(name);
    run("Copy");
    selectWindow(maskName);
    run("Paste");
    saveAs("Tiff", maskDir+name+"_mask");
    close( );
    close( );
    close( );
    close( );
    count++;
}
Macro step 2: measure cilia length:
//this macro requires the BoneJ plugin to be installed
files = getDirectory("Masks to analyze");
list = getFileList(files);
n = lengthOf(list);
count=0;
setBatchMode(false);
for(i=0;i<n;i++) {
    open(files+list[count]);
    x=getWidth( );
    y=getHeight( );
    maskName = getTitle( );
    Stack.setSlice(2);
    run("Copy");
    newImage("Untitled", "RGB black", x, y, 1);
    run("Paste");
    selectWindow(maskName);
    Stack.setSlice(2);
    run("Delete Slice");
    setTool("Wand");
    waitForUser("Choose the cilia, Shift+click OK to skip");
    if (isKeyDown("Shift") == true) {
        selectWindow(maskName);
        run("Close");
        selectWindow("Untitled");
        run("Close");
    }
    else {
    run("Make Inverse");
    run("Clear");
    run("Select None");
    run("Invert");
    run("Properties...", "unit=micron pixel_width=1 pixel_height=1");
    run("Thickness", "thickness graphic mask");
    processed = getTitle( );
    selectWindow("Results");
    saveAs("Results", files+"Cilia_length.xls");
    selectWindow(maskName);
    run("Close");
    selectWindow("Untitled");
    run("Close");
    selectWindow(processed);
    run("Close");
    count++;
    }
}
```

Results

Efficacy of Ex Vivo Reciliation:

Successful ciliogenesis was demonstrated in 14 of 15 independent experiments, achieving a success rate of over 90%. Results were highly reproducible, and the time from tracheal harvest to completion of ciliogenesis was only about 2 weeks. Freshly harvested and cleaned tracheas lined with ciliated epithelial cells beating in coordinated metachronal waves could be easily visualized. After pronase digestion, multiple clusters of tracheal ciliated epithelial cells disassociated from the trachea and floated in the medium with circular movements due to beating of motile cilia. Within 48 hours of stationary culture, large islands were established and grew rapidly, reaching confluence by about 7-10 days (FIGS. 1A-1F). After reaching confluence, collagen was removed, cells were washed and placed into suspension culture. Culture conditions were maintained, and cells were not fed again with suspension media. At about 7-9 days, ciliogenesis was complete and cells were ready for imaging. Most imaging occurred on Day 8.

Only 1-3 wells were needed per flask/group for suspension culture, thereby reducing the number of animals required for each experiment. In addition, two separate, independent experiments showed that pre-plating onto Primaria or regular culture dishes led to a significant reduction of fibroblast contamination. This was evidenced by a decrease in expression of fibroblast-specific protein (Fsp1), a marker of fibroblasts (Strutz, et al., *J. Cell Biol.*, 1995, 130:393-405), compared to control cells (p-value=0.0003). There was no significant difference in effectiveness of pre-plating using Primaria plates as compared to regular culture plates.

Human nasal epithelial cells were also cultured using a modification of the reciliation protocol used for the mouse trachea. As scraping the inferior turbinate leads to mostly single layer of ciliated cells, pronase digestion was not necessary. Cells were imaged, centrifuged, and placed into stationary culture (3 wells/sample of a 6-well plate). As the number of ciliated cells so obtained were significantly less than that recovered from an entire mouse trachea, growth to confluence took up to 3-4 weeks. However, time to reciliation was a similar 7-9 days once in suspension culture. Videomicroscopy was typically performed on Day 8.

siRNA Knockdown of Reciliation:

As a proof of principal, Dnai1, a gene responsible for outer dynein arms in motile cilia, was knocked down. Mutations in Dnai1 are known causes of PCD, a rare congenital disorder associated with motility defects of the respiratory epithelium, leading to recurrent pulmonary infections, chronic lung complications, and/or infertility due to immotile sperm (Shapiro, et al., *Pediatr. Pulmonol.*, 2016, 51:115-132). Scrambled siRNA was used as negative control. The disclosed protocol yielded robust reciliation in 100% (7/7) of control experiments using scrambled siRNA. In contrast, siRNA knockdown of Dnai1 showed significantly reduced reciliation with rare immotile cilia being present. Knock down of Dnai1 was confirmed 6 hours post siRNA knock down by real time PCR, showing a significant reduction in Dnai1 gene expression relative to scrambled siRNA (FIG. 3).

Effect of DAPT on Ciliogenesis:

The role of small molecules on ciliogenesis was assessed using the disclosed protocol. A dose response effect on ciliogenesis by the gamma-secretase inhibitor DAPT (N—[N-(3,5-Difluorophenacetyl)-L-alanyl]-S-phenylglycine t-butyl ester; Selleckchem, 52215) was evaluated. Mouse tracheal cells were harvested and grown to confluence in stationary media. After reaching 80-90% confluence, cells were treated with collagenase (200 IU/mL, Worthington, LS004210) to remove collagen, collected using a cell scraper, and suspended in suspension media containing identical volumes of DMSO having varying concentrations of DAPT: 2 nM, 20 nM, 200 nM and 2 μM of DMSO. A minimum of 8 videos were obtained per sample.

Figure 4A:
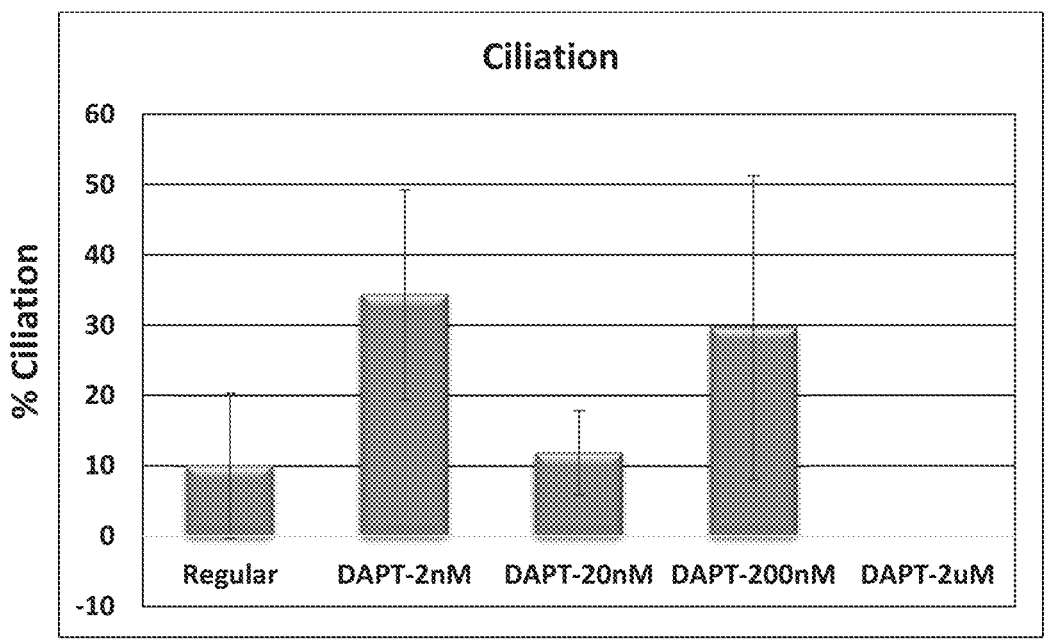
FIGS. 4(A-C) are graphs showing effects of DAPT on ciliogenesis of mouse tracheal epithelial cells (MTECs). Deciliated MTECs in stationary culture were treated with collagenase and transferred into suspension culture containing 0 nM DAPT ("regular" media), or media containing the indicated increasing amounts of DAPT. The percent ciliation (FIG. 4A), cilia length (FIG. 4B), and cilia beat frequency (FIG. 4C) were determined from cell micrographs, as described in FIGS. 2(A-C). Error bars represent ±1 SD. Results between 2 nM DAPT-treated cells and untreated cells were significant for all three variables measured. 2 µM DAPT was toxic to cells, resulting in extensive cell debris, cell death and essentially no ciliated cells which could be measured.
Figure 4B:
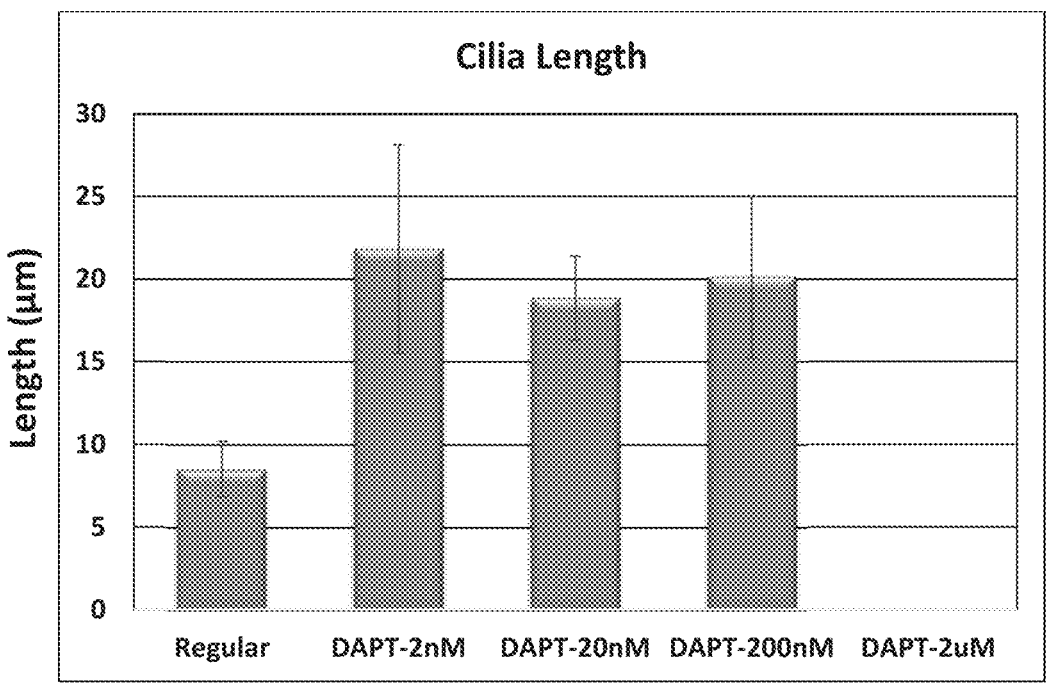
Figure 4C:
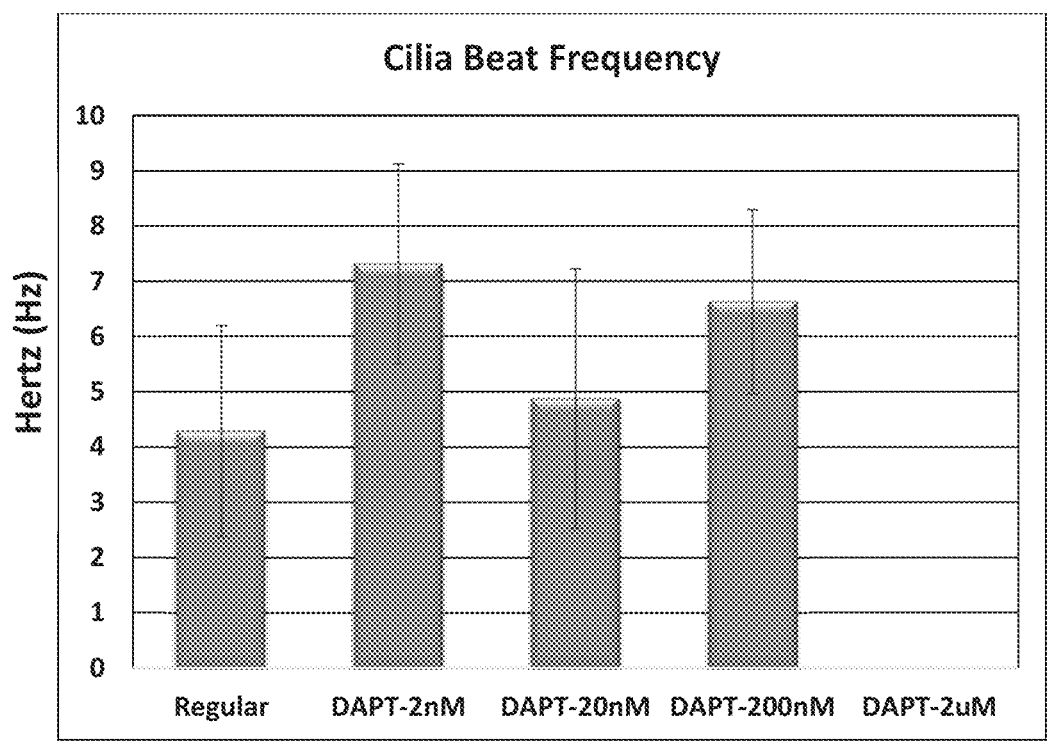

DAPT at concentrations of 2 μM or more were toxic to cells, leading to cell death with very few if any ciliated cells. This was not an effect of DMSO, the vehicle for DAPT, as DMSO volumes were constant. However, a much lower concentration of DAPT, 2 nM, resulted in almost 3-fold increased ciliogenesis over baseline (FIG. 4A). In addition to enhancing reciliation, cilia length (FIG. 4B) and cilia beat frequency (FIG. 4C) were significantly increased with 2 nM DAPT.

Figure 5A:
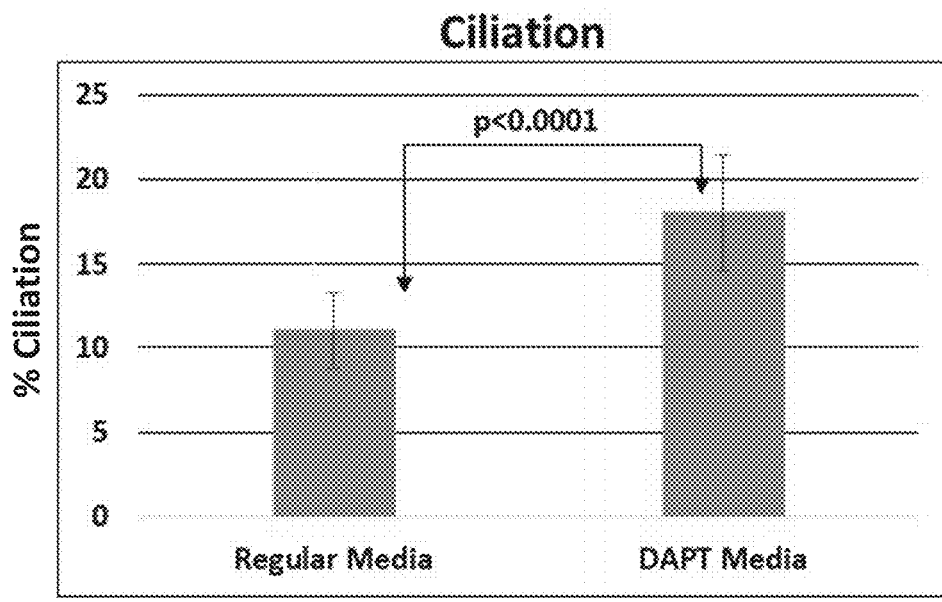
FIGS. 5(A-C) are graphs showing effect of 2 nM DAPT on ciliogenesis of human nasal epithelial cells from 12 subjects with congenital heart defects. Compared to 0 nM DAPT ("regular media"), 2 nM DAPT treatment resulted in significant increases in percent ciliation (FIG. 5A), cilia length (FIG. 5B), and cilia beat frequency (FIG. 5C). Error bars represent±1 SD.
Figure 5B:
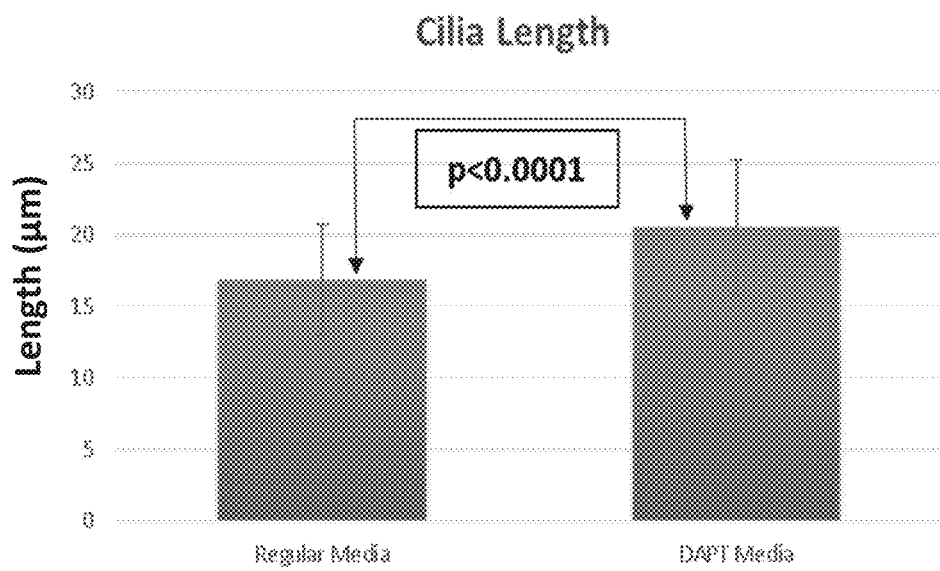
Figure 5C:
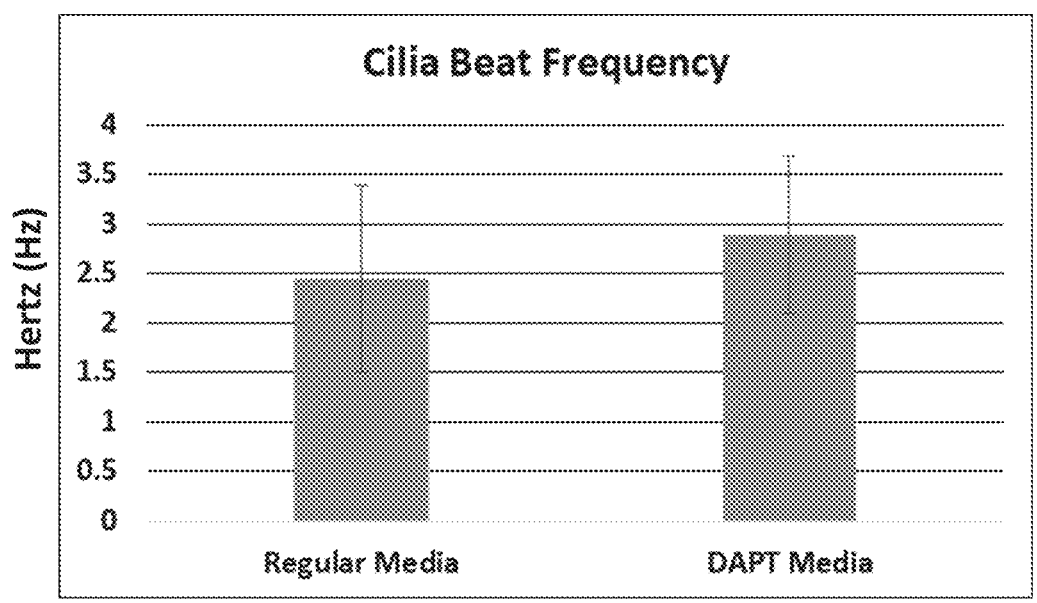
Figure 6A:
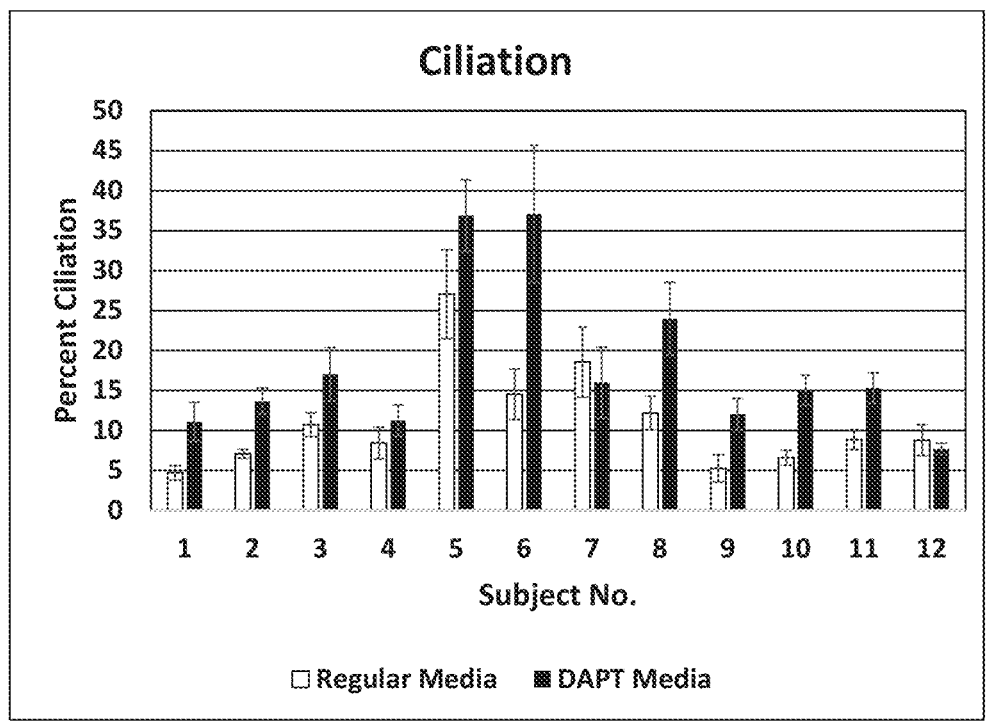
FIGS. 6(A-C) are graphs showing the raw data for percent ciliation (FIG. 6A), cilia length (FIG. 6B), and cilia beat frequency (FIG. 6C) of human nasal epithelial cells from each of the 12 subjects referred to in FIGS. 5(A-C). Cells of each subject were treated with 0 nM DAPT ("regular media" or control) or 2 nM of DAPT.
Figure 6B:
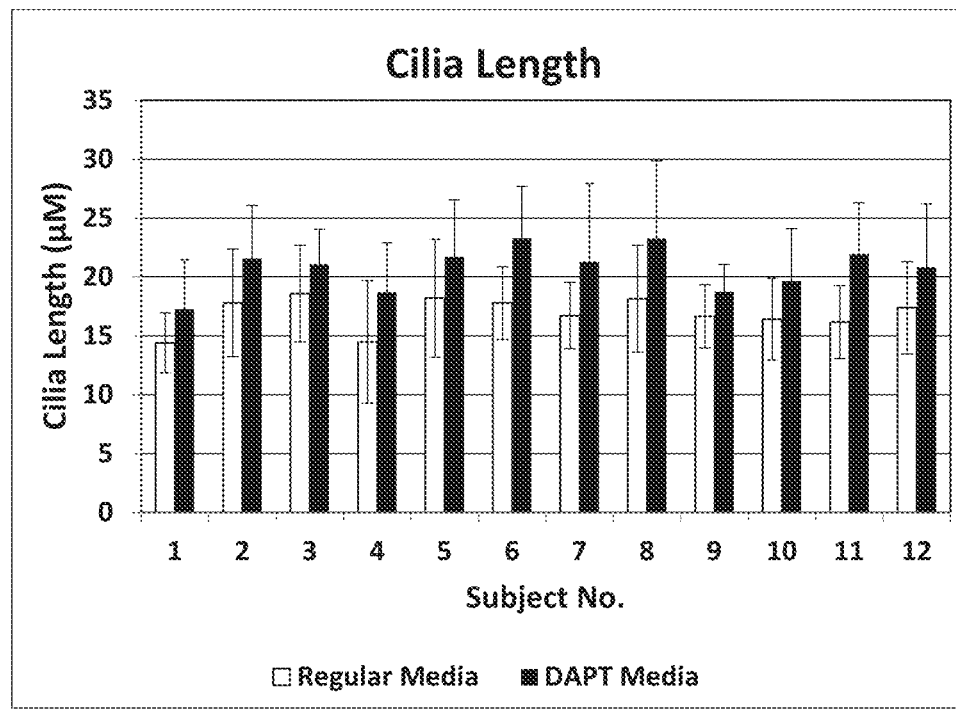
Figure 6C:
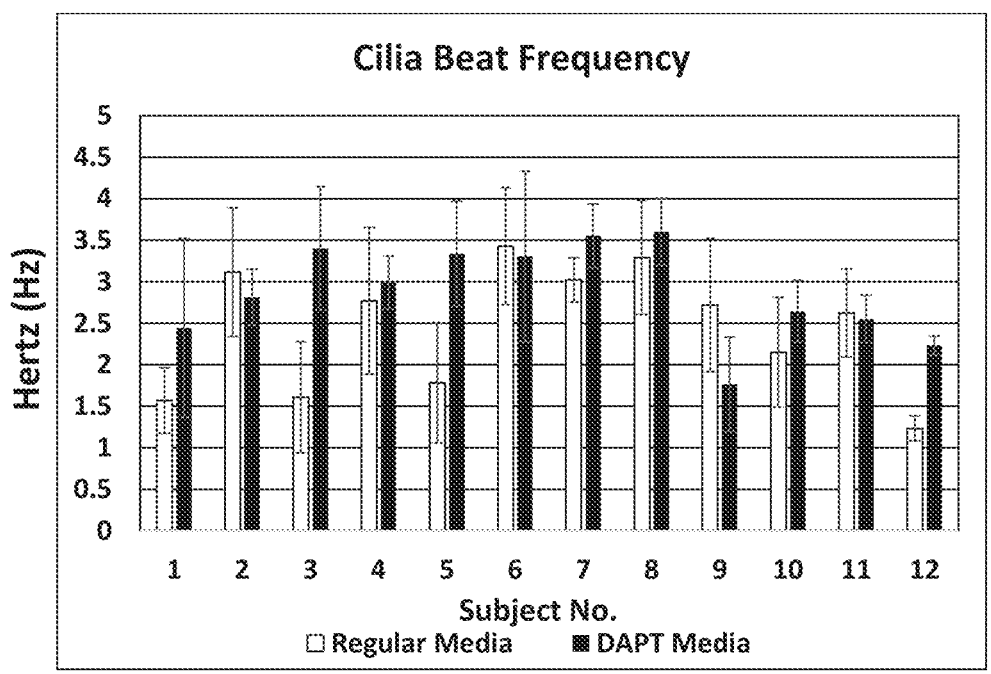
Figure 7A:
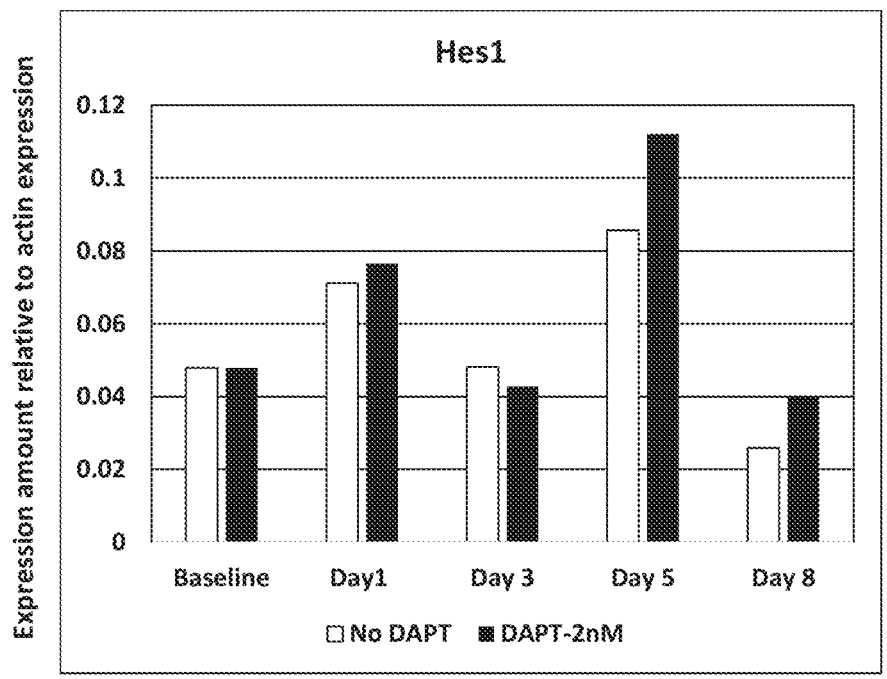
FIGS. 7(A-I) are graphs showing quantitative PCT (qPCR) of gene expression in mouse tracheal epithelial cells during ciliogenesis. Cells were grown to confluence in stationary culture, treated with collagenase, then placed into suspension culture having 0 nM or 2 nM DAPT, which marked the "baseline" time point. At the indicated times, qPCR experiments were performed to detect gene expression of Hes1 (FIG. 7A), Hes5 (FIG. 7B), Hey1 (FIG. 7C), Psen1 (FIG. 7D), Hif1α (FIG. 7E), Notch1 (FIG. 7F), nNOS (FIG. 7G), iNOS (FIG. 7H), and eNOS (FIG. 7I).
Figure 7B:
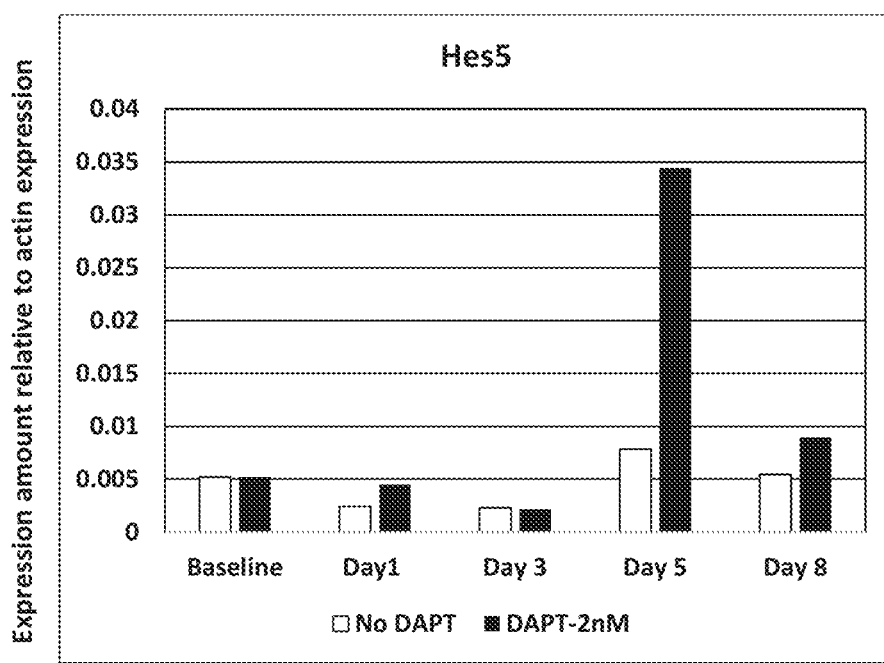
Figure 7C:
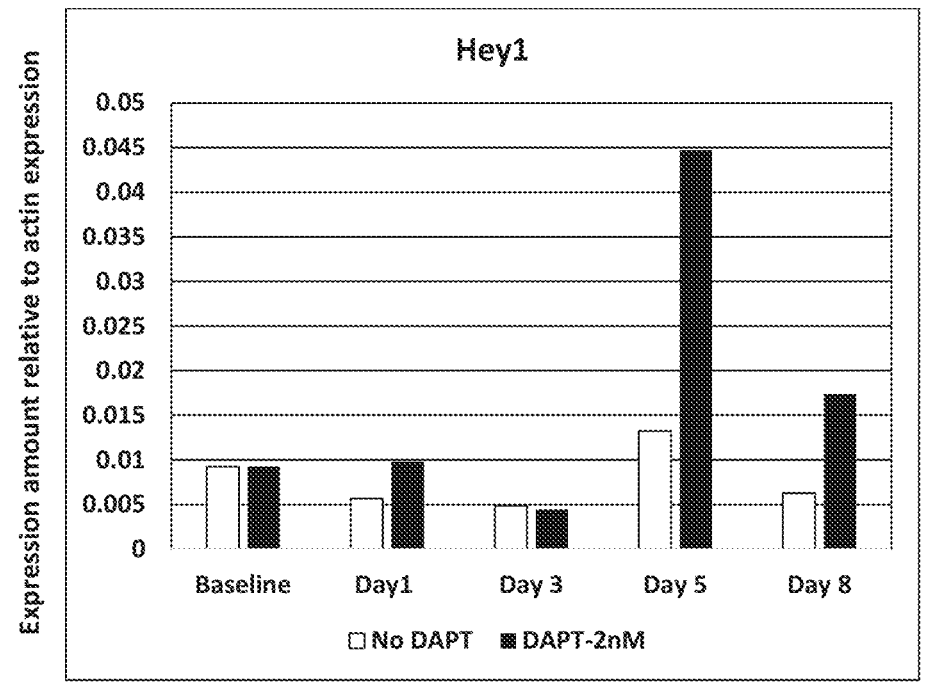
Figure 7D:
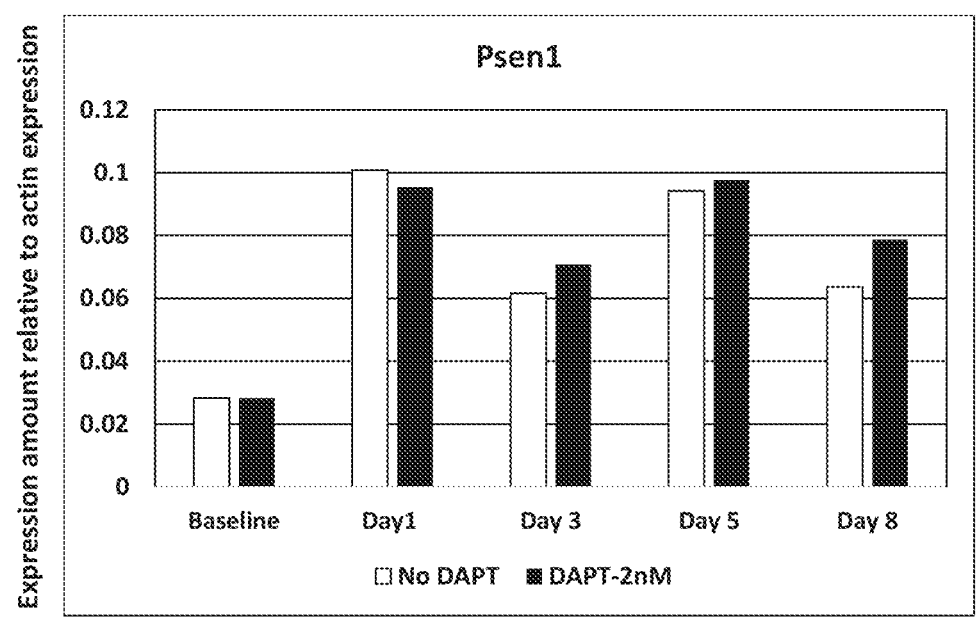
Figure 7E:
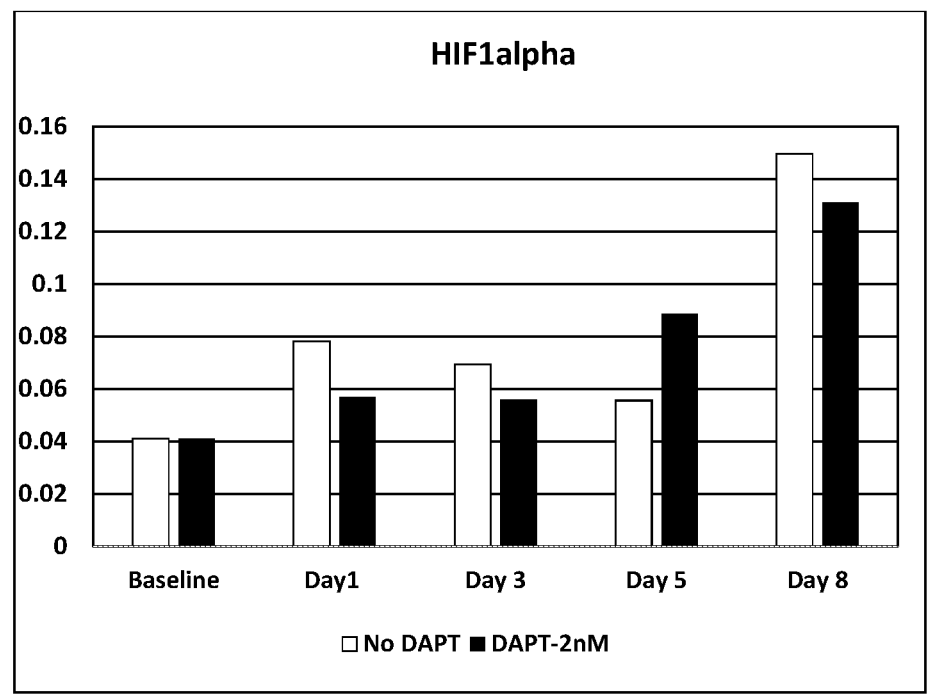
Figure 7F:
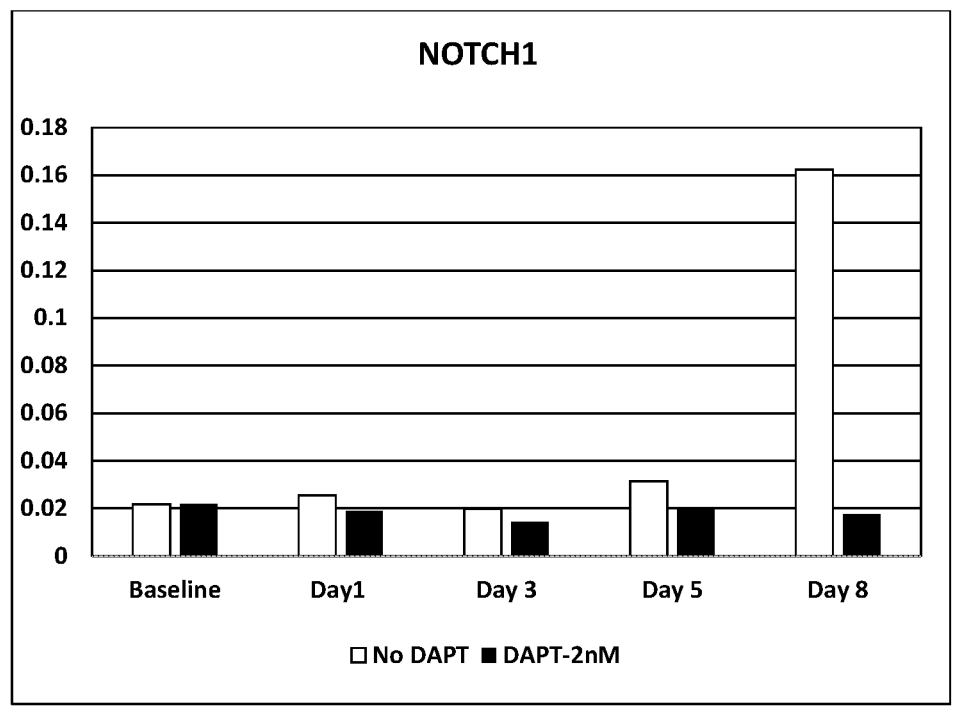
Figure 7G:
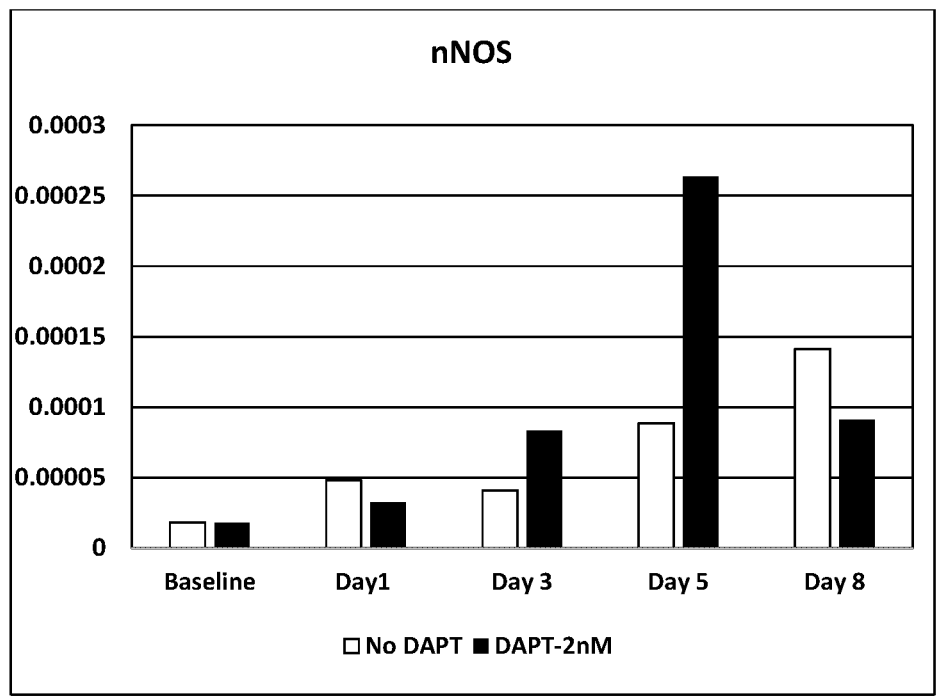
Figure 7H:
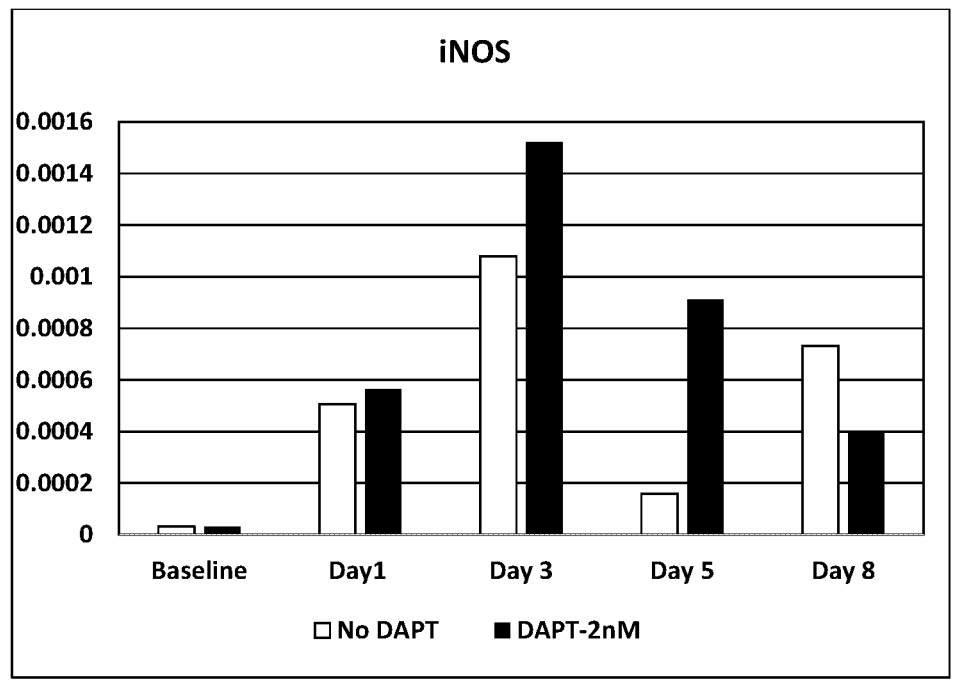
Figure 7I:
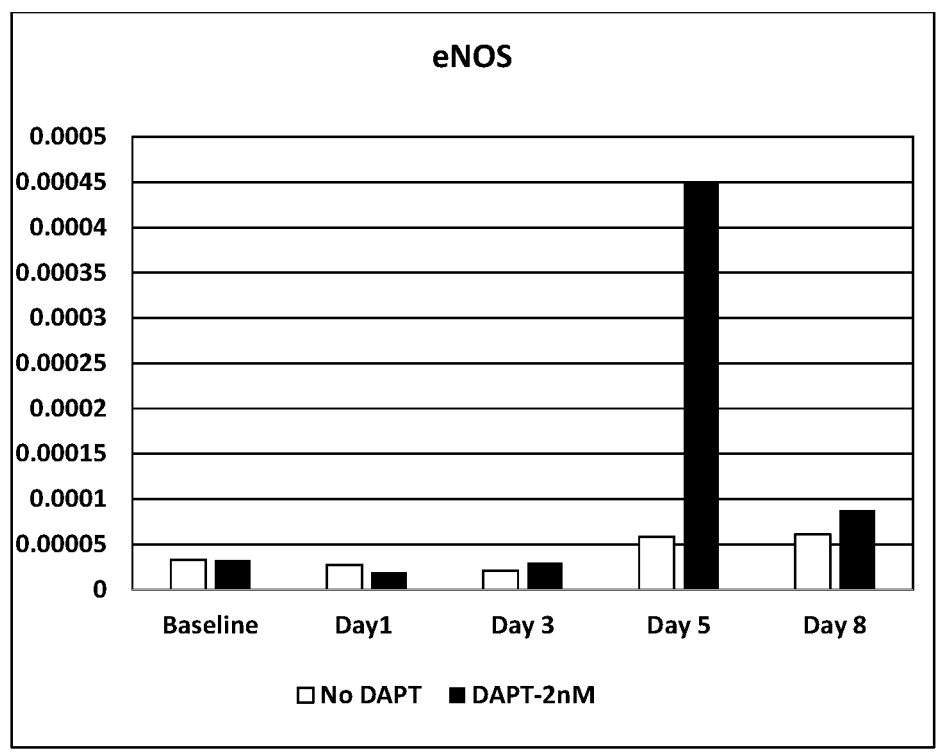

With minor modifications, the protocol was applied to culture and reciliation of human nasal epithelial cells. 2 nM DAPT in human nasal epithelial culture resulted in a significantly greater percentage reciliation compared to regular media in 12 paired samples (with and without 2 nM DAPT) from subjects with congenital heart defects, consistent with effect observed in mouse tracheal epithelial cell cultures (FIG. 5A). In addition, both cilia length (FIG. 5B) and cilia beat frequency (FIG. 5C) were significantly increased with 2 nM DAPT treatment. Individual subject data, paired with (2 nM) and without (0 nM) DAPT, are presented in FIGS. 6A-6C.

Because 2 nM DAPT treatment significantly improved several parameters of ciliogenesis (percent ciliation, cilia length, and cilia beat frequency), quantitative PCR (qPCR) experiments were used to determine whether DAPT affected expression of genes involved in ciliogenesis. Indeed, expression of multiple genes such as Hes1, Hes5, Hey1, Notch1, Psen1, Hif1α, nNOS, iNOS, and eNOS was altered at varying time points during ciliogenesis in suspension culture containing 2 nM DAPT, as compared to untreated (no DAPT) controls (FIGS. 7A-7J). These results show DAPT affects expression of genes involved in ciliogenesis, most prominently at day 5 just prior to ciliation, as very small immotile cilia begin to appear at day 6, which likely contributes to the ciliogenesis-promoting effects of DAPT. This effect was most marked for the three isoforms of nitric oxide synthase (NOS).

Example 2: Administration of DAPT to Modify Ciliogenesis in the Airways In Vivo

DAPT treatment results in improved ciliogenesis characterized in part by production of longer and faster beating cilia and increased number of cilia, thereby increasing mucociliary clearance in chronic respiratory conditions like asthma and chronic obstructive pulmonary diseases or COPD. These diseases are exemplified by increased mucus production, reduced ciliated surfaces, and shorter cilia, all of which contribute to chronic respiratory pathologies like chronic cough, recurrent infections and bronchospasm. Changing cell behavior decreases mucus production, increases ciliogenesis, and/or increases mucociliary clearance, thereby treating the underlying pathogenesis of these chronic conditions.

Ten subjects are diagnosed with Chronic Obstructive Pulmonary Disease (COPD). Each subject provides informed consent regarding providing epithelial cell samples and to receiving a blinded treatment of either DAPT or a control placebo. Nasal brushing of the inferior nasal turbinate with a nasal curette is used to obtain airway epithelial cells from each subject. The epithelial cells are placed into suitable medium such as Leibovitz-15 medium. Thereafter, cell samples are evaluated for percentage ciliation, cilia length, and/or cilia beat frequency by video-microscopy, and the results are recorded. Video-microscopy confirms each subject has epithelial cells which are reduced in cilia number, cilia length, and/or cilia beat frequency compared to averages or standards present in the medical literature.

DAPT is inhalationally administered to five of the subjects via a nebulizer or an inhaler (hereinafter, "DAPT-treated subjects"). Placebo water vapor is inhalationally administered via a nebulizer or an inhaler to the remaining five subjects not treated with DAPT (hereinafter, "control-treated subjects"). An array of dosages and dosing schedules can be selected, however in the present study, the subjects are inhalationally administered approximately 1 mg DAPT per kg body weight (or placebo) once per day for seven days.

On day eight, epithelial cells are obtained from the airways of each subject by nasal brushing of the inferior nasal turbinate with a nasal curette. The epithelial cells are placed into suitable medium such as Leibovitz-15 medium. Thereafter, cell samples are evaluated for percentage ciliation, cilia length, and/or cilia beat frequency by video-microscopy, and the results are recorded. Video-microscopy confirms each of the five DAPT-treated subjects has epithelial cells which are increased in cilia number, cilia length, and/or cilia beat frequency as compared to both 1) the epithelial cells of placebo-treated subjects, and 2) the pre-treatment measurements recorded for epithelial cells of each respective DAPT-treated subject. Further, some of the DAPT-treated subjects report that one or more symptoms of their COPD (e.g., coughing) have ameliorated.

Example 3: Administration of DAPT to Modify Ciliogenesis in Neurological Tissue In Vivo As with respiratory conditions in Example 2, treatment with DAPT improves ciliogenesis in ciliated cells of neurological tissue. For instance, ependymal cells can contain cilia which facilitate the flow of cerebral spinal fluid, which can be enhanced by production of longer and faster beating cilia and greater number of cilia, thereby avoiding complications such as fluid retention in the brain resulting in e.g., hydrocephalus.

Ten subjects are diagnosed with hydrocephalus. Each subject provides informed consent regarding providing epithelial cell samples and to receiving a blinded treatment of either DAPT or a control placebo. Intrathecal biopsy is used to obtain ependymal cells from the cerebrospinal fluid of each subject. The ependymal cells are placed into suitable medium such as Leibovitz-15 medium. Thereafter, cell samples are evaluated for percentage ciliation, cilia length, and/or cilia beat frequency by video-microscopy, and the results are recorded. Video-microscopy confirms each subject has ependymal cells which are reduced in cilia number, cilia length, and/or cilia beat frequency compared to averages or standards present in the medical literature.

DAPT is intrathecally administered to five of the subjects via an intrathecal syringe (hereinafter, "DAPT-treated subjects"). Placebo composition is intrathecally administered via an intrathecal syringe to the remaining five subjects not treated with DAPT (hereinafter, "control-treated subjects"). An array of dosages and dosing schedules can be selected; however, in the present study, the subjects are intrathecally administered approximately 1 mg DAPT per kg body weight (or placebo) only once.

On day eight post-injection, ependymal cells are obtained from the cerebrospinal fluid of each subject by intrathecal biopsy. The ependymal cells are placed into suitable medium such as Leibovitz-15 medium. Thereafter, cell samples are evaluated for percentage ciliation, cilia length, and/or cilia beat frequency by video-microscopy, and the results are recorded. Video-microscopy confirms each of the five DAPT-treated subjects has ependymal cells which are increased in cilia number, cilia length, and/or cilia beat frequency as compared to both 1) the ependymal cells of placebo-treated subjects, and 2) the pre-treatment measurements recorded for ependymal cells of each respective DAPT-treated subject. Further, some of the DAPT-treated subjects report that one or more symptoms of their hydrocephalus (e.g., headache) have ameliorated.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for modifying ciliogenesis in one or more cells of a subject, the method comprising administering to the subject in need thereof an effective amount of a composition comprising a Notch signaling inhibitor, wherein the modification results in an increase in a number of cilia, an increase in a length of cilia, and/or an increase in a beat frequency of cilia as compared to a control and wherein the effective amount is from 0.1 µg/kg body weight to 100 µg/kg body weight.

2. The method of claim 1, wherein the number of cilia on the one or more cells is increased by at least 25%.

3. The method of claim 1, wherein the length of cilia is increased by at least 20%.

4. The method of claim 1, wherein the beat frequency of cilia is increased by at least 15%.

5. The method of claim 1, wherein the Notch signaling inhibitor comprises a gamma secretase inhibitor or a Recombination Signal Binding Protein for Immunoglobulin Kappa J Region (RBP-Jκ) inhibitor.

6. The method of claim 5, wherein the gamma-secretase inhibitor is selected from the group consisting of a dipeptide class, sulfonamide class, transition state mimic class, benzodiazepine class, benzocaprolactam class, and combinations thereof.

7. The method of claim 1, wherein the Notch signaling inhibitor is selected from the group consisting of (N-[N-(3,5-difluorophenacetyl-L-alanyl)]-S-phenylglycine t-butyl ester) (DAPT), 1-(S)-endo-N-(1,3,3)-trimethylbicyclo[2.2.1]hept-2-yl)-4-fluorophenyl sulfonamide, WPE-III31C, S-3-[N'-(3,5-difluorophenyl-alpha-hydroxyacetyl)-L-alanilyl] amino-2,3-dihydro-1-methyl-5-phenyl-1H-1,4-benzodiazepin-2-one, (N)[(S)-2-hydroxy-3-methyl-butyryl]-1-(L-alaninyl)-(S)-1-amino-3-methyl-4,5,6,7-tetrahydro-2H-3-benzazepin-2-one, and combinations thereof.

8. The method of claim 1, wherein the increase in the number of cilia, the increase in the length of cilia, and/or the increase in the beat frequency of cilia is achieved in nine days or less.

9. The method of claim 1, wherein the one or more cells are epithelial cells.

10. The method of claim 1, wherein the one or more cells of the subject comprises a multitude of cells of the subject, and wherein the increase in the number of cilia, the increase in the length of cilia, and/or the increase in the beat frequency of cilia is determined based on an average obtained from the multitude of cells.

11. The method of claim 1, wherein the subject is a human.

12. The method of claim 1, wherein the subject has chronic obstructive pulmonary disorder (COPD), emphysema, asthma, primary ciliary dyskinesia (PCD), cystic fibrosis (CF), or hydrocephalus.

13. The method of claim 1, wherein 0.1 µg/kg of a Notch signaling inhibitor is administered to the subject.

14. The method of claim 13, wherein the Notch signaling inhibitor is DAPT.

15. The method of claim 1, wherein 1 µg/kg of a Notch signaling inhibitor is administered to the subject.

16. The method of claim 15, wherein the Notch signaling inhibitor is DAPT.

17. The method of claim 1, wherein 10 µg/kg of a Notch signaling inhibitor is administered to the subject.

18. The method of claim 17, wherein the Notch signaling inhibitor is DAPT.

19. The method of claim 1, wherein 100 µg/kg of a Notch signaling inhibitor is administered to the subject.

20. The method of claim 19, wherein the Notch signaling inhibitor is DAPT.

* * * * *